United States Patent
Eason et al.

(10) Patent No.: US 8,474,453 B2
(45) Date of Patent: Jul. 2, 2013

(54) INHALER

(75) Inventors: Stephen William Eason, Diss (GB); Matthew Sarkar, Cambridge (GB); Graham Gibbins, Holt (GB); Nicholas John Campling, Peterborough (GB); Howard William Biddle, Histon (GB); Tristian Roger Thornhill, Peterborough (GB); Duncan James Bradley, Ewhurst (GB)

(73) Assignee: Vectura Delivery Devices Limited (GB)

( * ) Notice: Subject to any disclaimer, the term of this patent is extended or adjusted under 35 U.S.C. 154(b) by 1071 days.

(21) Appl. No.: 11/881,582

(22) Filed: Jul. 27, 2007

(65) Prior Publication Data
US 2009/0007908 A1    Jan. 8, 2009

(30) Foreign Application Priority Data
Jul. 6, 2007    (EP) .................................... 07111998

(51) Int. Cl.
*A61M 15/00* (2006.01)
*B65D 83/06* (2006.01)

(52) U.S. Cl.
USPC ............. 128/203.15; 128/203.12; 128/203.21

(58) Field of Classification Search
USPC .......... 128/203.15, 203.21, 203.12; 267/36.1; 604/58; 222/81, 83, 85, 87, 144
See application file for complete search history.

(56) References Cited

U.S. PATENT DOCUMENTS

| | | | | |
|---|---|---|---|---|
| 3,425,119 A | * | 2/1969 | Holtfreter | 29/593 |
| 4,733,797 A | * | 3/1988 | Haber | 221/8 |
| 5,337,740 A | * | 8/1994 | Armstrong et al. | 128/203.12 |
| 5,590,645 A | * | 1/1997 | Davies et al. | 128/203.15 |
| 6,073,814 A | * | 6/2000 | Fuchs | 222/321.1 |
| 6,502,454 B1 | * | 1/2003 | Macioce et al. | 73/146 |
| 6,725,857 B2 | * | 4/2004 | Ritsche | 128/200.14 |
| 7,424,888 B2 | * | 9/2008 | Harvey et al. | 128/203.15 |
| 7,805,790 B2 | * | 10/2010 | DeMoss | 5/716 |
| 2001/0020147 A1 | * | 9/2001 | Staniforth et al. | 604/58 |
| 2005/0005934 A1 | * | 1/2005 | Harvey | 128/203.15 |
| 2005/0019224 A1 | * | 1/2005 | Pechter et al. | 422/102 |
| 2005/0039743 A1 | * | 2/2005 | Taylor | 128/203.15 |
| 2006/0196504 A1 | * | 9/2006 | Augustyn et al. | 128/203.15 |

(Continued)

FOREIGN PATENT DOCUMENTS

| | | |
|---|---|---|
| JP | 04-220266 | 11/1992 |
| JP | 2006-528500 | 12/2006 |

(Continued)

OTHER PUBLICATIONS

European Search Report dated Jun. 20, 2008 which was issued in connection with corresponding European Patent Application No. 07 11 1998.

(Continued)

*Primary Examiner* — Justine Yu
*Assistant Examiner* — Valerie L Skorupa
(74) *Attorney, Agent, or Firm* — Davidson, Davidson & Kappel, LLC

(57) ABSTRACT

An inhaler is disclosed. The inhaler has a housing to receive an elongate strip of blisters each containing a dose of medicament and being sequentially movable into alignment with means for breaching a blister to enable a user to inhale said dose contained therein. The device has a spiral wound element within the housing that receives and coils said strip of blisters that have been breached.

12 Claims, 19 Drawing Sheets

U.S. PATENT DOCUMENTS

| | | | |
|---|---|---|---|
| 2007/0062525 A1* | 3/2007 | Bonney et al. | 128/203.21 |
| 2007/0137645 A1* | 6/2007 | Eason et al. | 128/203.15 |
| 2008/0142008 A1 | 6/2008 | Pocock et al. | |
| 2009/0078252 A1* | 3/2009 | Anderson et al. | 128/202.22 |
| 2009/0139516 A1* | 6/2009 | Augustyn et al. | 128/200.23 |
| 2010/0037894 A1* | 2/2010 | Rouse et al. | 128/203.15 |
| 2010/0139654 A1* | 6/2010 | Thoemmes et al. | 128/203.15 |

FOREIGN PATENT DOCUMENTS

| | | |
|---|---|---|
| WO | WO 02/36189 | 5/2002 |
| WO | WO 03/035508 | 5/2003 |
| WO | WO 2005/014089 | 2/2005 |
| WO | WO 2005-014089 A1 | 2/2005 |
| WO | WO 2005/037353 A1 * | 4/2005 |
| WO | WO 2006-079751 A1 | 8/2006 |

OTHER PUBLICATIONS

Office Action from the Japanese Intellectual Property Office, dated Oct. 30, 2012, issued in connection with corresponding Japanese Patent Application No. 2010-514015.

* cited by examiner (a)

(b)

INHALER

FIELD OF THE INVENTION

The present invention relates to an inhalation device for oral or nasal delivery of medicament in powdered form and to an inhaler containing a strip of blisters each having a breachable lid and/or base that contains a dose of medicament for inhalation by a user of the device.

BACKGROUND OF THE INVENTION

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs thereby avoiding the need for hypodermic injections.

DETAILED DESCRIPTION OF THE INVENTION

It is common for dry powder formulations to be pre-packaged in individual doses, usually in the form of capsules or blisters which each contain a single dose of the powder which has been accurately and consistently measured. A blister is generally cold formed from a ductile foil laminate or a plastics material and includes a puncturable or peelable lid which is heat-sealed around the periphery of the blister during manufacture and after introduction of the dose into the blister. A foil blister is preferred over a polymer blister or gelatine capsule as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

Inhalation devices that receive a blister pack comprising a number of blisters each of which contain a pre-metered and individually packaged dose of the drug to be delivered are known. Actuation of the device causes a mechanism to breach or rupture a blister, such as by puncturing it or peeling the lid off, so that when the patient inhales, air is drawn through the blister entraining the dose therein that is then carried out of the blister through the device and via the patient's airway down into the lungs. Pressurized air or gas or other propellants may also be used to carry the dose out of the blister. Alternatively, the mechanism that punctures or opens the blister may also push or eject the dose out of the blister into a receptacle from which the dose may subsequently be inhaled.

It is advantageous for the inhaler to be capable of holding a number of doses to enable it to be used repeatedly over a period of time without the requirement to open and/or insert a blister into the device each time it is used. Therefore, many conventional devices include means for storing a number or strip of blisters each containing an individual dose of medicament. When a dose is to be inhaled, an indexing mechanism moves a previously emptied blister away from the opening mechanism so that a fresh one is moved into a position ready to be opened for inhalation of its contents.

An inhaler of the type described above is known from the Applicant's own co-pending international application no. PCT/GB2004/004416 filed on 18 Oct. 2004 and claiming priority from GB application no. 0324358.1 filed 17Oct. 2003. This international application has been published as WO 2005/037353 A1.

According to one embodiment described and claimed in WO 2005/037353 A1, and illustrated in FIGS. 1*a* and 1*b* of the accompanying drawings, an inhaler 1 has a housing 2 containing a coiled strip of blisters 3. An indexing mechanism 4 comprising a single actuating lever 5 unwinds the coil 3 one blister at a time so that they pass over a blister locator chassis 6 and successively through a blister piercing station 7, when the actuator 5 is pivoted in a direction indicated by arrow "A" in FIG. 1*b*. The blister 3*a* located at the blister piercing station 7 on each movement of the actuator 5 is pierced on the return stroke of the actuator 5 (in the direction indicated by arrow "B" in FIG. 1*b*) by piercing elements 8 on the actuator 5 itself so that, when a user inhales through a mouthpiece 9, an airflow is generated within the blister 3*a* to entrain the dose contained therein and carry it out of the blister 3*a* via the mouthpiece 9 and into the user's airway.

Although the inhalation device referred to above and described in the aforementioned publication has addressed many of the known problems associated with these types of devices, it is designed so as to store only a small number of used blisters within the device so that, when that number of blisters is exceeded, they extend out of the housing of the device so that the user must separate those used blisters from those unused blisters that remain within the device and discard the detached portion of the strip. The direction of movement of the used blisters is indicated by arrow "C" in FIGS. 1*a* and 1*b*. The blister strip 3 may be perforated or weakened between each or a number of blisters to facilitate the tearing of used blisters from the strip 3.

Although devices that eject used blisters have the advantage of being particularly small and lightweight, it is desirable to provide a fully integrated device in which all the used blisters are retained within the device so that separation of used blisters from those that remain in the device is no longer necessary. Not only would this make the device simpler to use because the user no longer has to concern themselves with periodic detachment and disposal of a used portion of the blister strip but any potential contamination of the fingers by residual drug remaining on the used blisters can be avoided because there is no need for the user to come into contact with any of the used blisters. Therefore, the entire strip can be effectively sealed within the housing of the device.

Used blisters can be simply wound around a take-up spool within the device. However, such devices are large and require means to rotate the spool to wind up the used blisters. The leading end of the strip must also be pre-attached to the spool so that the strip starts to wind around the spool as the spool is rotated.

WO 2005/037353 also discloses an embodiment in which all the blisters are retained within the device and in which the blister strip takes the form of an endless loop that is wrapped around itself. Such a device 10 is shown in FIG. 2. If suitable low friction materials are used, the two centre spools 11,12 need not be driven, the drive being solely provided by the indexing mechanism 4 that is concentric with the actuator pivot and which rotates in response to pivotal movement of the actuator 13 by the user, as described with reference to the device shown in FIGS. 1*a* and 1*b*. Although this device provides a compact arrangement, if the strip 14 is too long it tends to jam on the walls 15 separating the elements of the strip 14 in the manner of a wrap-spring clutch or a rope passed around a cylinder preventing proper indexing of the strip 14.

A previously undisclosed version of a loop type device 20 is shown in FIGS. 3*a* and 3*b* in which the inherent potential for jamming is minimized by providing drive to successive parts 21 of the strip 22 at several points along its length. As shown in the rear view of FIG. 3a, the loop 22 follows a serpentine path around a number of wheels 7, at least some of which are driven from the main indexing wheel 4, the remaining wheels being idler wheels 8 which guide the successive parts of the strip 21 of the loop 22. In the front view of FIG. 3b, it can be seen that the indexing mechanism 4 and the three secondary driving wheels 7 are toothed and are geared to a single larger toothed gear wheel 23 mounted for rotation on a central spindle 24 on the rear of the housing 25.

The present invention seeks to provide an inhalation device that retains a used strip of blisters within the housing of the device whilst maintaining simplicity and compactness of the device, as well as ease of use.

Although the device may be disposable after all the blisters contained within it have been exhausted, it is envisaged that it may be possible to open the housing to enable the old strip to be removed and a fresh one inserted. It is also envisaged that blisters may be retained within a portion of the housing of the device which is detachable from the remainder of the housing in which the indexing and piercing mechanism is located, thereby forming a replaceable cartridge. This would enable an exhausted blister strip to be removed without direct contact by the patient.

A potential complication with inhalation devices that retains used blisters is that a small amount of the powdered dose, typically between 1%-5%, may remain in each blister after inhalation. Furthermore, if a patient indexes the strip without having previously inhaled the dose in a blister that has been pierced or breached, the amount of residual powder will be substantial. It is therefore important to prevent the unused blisters from becoming contaminated with loose powder that could have a detrimental effect on the operation of the device and also result in the patient exceeding an intended dose as they may inhale some of the residual powder as well as the contents of a pierced blister. Furthermore, if the residual powder has been exposed to the atmosphere, it may have also degraded making it unsuitable for inhalation.

In view of the foregoing, the present invention also seeks to address the problem of residual powder containment to prevent residual powder from contaminating unused blisters remaining in the device and from being inhaled by a user of the device.

According to one aspect of the invention, there is provided an inhaler comprising a housing to receive a strip of blisters each containing a dose of medicament and means to sequentially move each blister into alignment with means for opening a blister to enable a user to inhale said dose and, a spiral wound element or former to coil said strip.

Preferably, the spiral wound element is configured so that a used portion of the strip, which is made up of blisters which have been aligned with the means for opening a blister, is gradually coiled within the spiral wound element as the device is used.

In one embodiment, the spiral wound element is rigid. However, in a more preferable embodiment, the spiral wound element is formed from a flexible material.

The spiral wound element may be formed from a deformable non-resilient material.

However, in a preferred embodiment it is formed from a resilient deformable material.

The resiliency of the spiral wound element is preferably selected in dependence on the stiffness of a used portion of a blister strip so that a first closed coil of a used portion of a blister strip is formed in the spiral wound element prior to any substantial deformation or expansion of the spiral wound element. Alternatively the configuration of a more resilient spiral wound element can be arranged such that a first closed coil is formed during initial deflection of the element.

In one preferred embodiment, the spiral wound element is configured so that it expands radially as the length of the used blister strip coiled within it increases as more blisters are breached.

Conveniently, the spiral wound element has at least one winding that extends over 360 degrees.

The stiffness of the spiral wound element may advantageously vary along at least a portion of its length. In particular, the stiffness of the spiral wound element may decrease towards its inner end.

One approach to achieving the reduction in stiffness is for the thickness of the spiral wound element to gradually reduce towards its inner end and/or its width to gradually reduce towards its inner end.

In one embodiment, holes, slots or other apertures are formed in the spiral wound element close to or at its inner end.

The spiral wound element may be formed for example from phosphor bronze, stainless steel, titanium, spring steel, shape memory alloy, nylon, acetal, PTFE or polypropylene.

The spiral wound element may also be coated with a low friction material to aid smooth winding of the breached blister strip, for example, a PTFE coating. Alternatively the surface finish or texture of the spiral wound element can be selected to provide a low friction surface.

The spiral wound element can be formed from flat strip material, or from square, circular or rectangular section material. Alternatively, the spiral may be formed from one or more wire elements wound into a spiral. This reduces the contact area with the strip and therefore reduces friction.

The materials and components may be used separately or in combination to give the desired characteristics.

In a preferred embodiment, the spiral wound element is a coil spring formed from a thin sheet of material.

According to one aspect of the invention, there is provided a housing to receive a strip of blisters each containing a dose of medicament and means to sequentially move each blister into alignment with means for opening a blister to enable a user to inhale said dose, the inhaler having a first compartment to contain unused blisters and a second compartment to receive used blisters, the first and second compartments being separated by a flexible and/or movable dividing wall.

Preferably, an aperture is provided in the flexible and/or movable dividing wall for the passage of the blister strip from the first compartment into the second compartment, said aperture including means to prevent the egress of powdered medicament from the used blister compartment in to the unused blister compartment through the aperture. The means may be a brush or elastomeric element.

Although the unused blister strip and the breached blisters may be housed in separate compartments, in one embodiment the housing comprises a common chamber to receive both an unused and a used portion of the blister strip.

Advantageously, the chamber is configured so that the used portion of the strip occupies a region of the chamber initially occupied by an unused portion of the blister strip as the size of the used portion of the strip increases.

In one embodiment, the dividing wall may be rigid but configured so as to be slideable within the housing so that the relative sizes of the unused and used blister compartments can be altered.

The flexible dividing wall may be fixed to the housing at one or both ends and may comprise a foam strip which can include a stiffening element. In one embodiment, the flexible dividing wall is movable and fixed to the housing at one end so as to pivot about said end within the housing.

In one embodiment, the flexible and/or movable dividing wall is flexible and configured so that it extends across said space between said sidewalls of the inhaler to prevent passage of powdered dose between the unused and used blister compartments. In one embodiment, the flexible dividing wall is at least partially attached to the spiral wound element.

The flexible dividing wall can also be designed to exert a constraining or steadying force on one or both of the blister coils. This constraining force can be achieved by, for example, the stiffness of the dividing wall or by the friction created as the dividing wall slides relative to the walls of the housing. This can be particularly beneficial if the spiral wound element containing the used portion of the blister coil is selected to be very resilient, and can help to ensure that the coil of used blisters is kept as small as possible.

In one embodiment, the inhaler may comprise a second spiral wound element within which an unused blister strip may be coiled up within said housing such that the second spiral wound element retracts as the first spiral wound element expands, as the size of the coil formed from a used portion of the strip increases and the size of the coil forming the unused portion of the strip decreases.

According to another aspect of the invention, there is provided an inhaler comprising a housing to receive a strip of blisters each containing a dose of medicament and means to sequentially move each blister into alignment with means for opening a blister to enable a user to inhale said dose, wherein the housing comprises a common chamber to receive an unused blister strip and, a used portion of that strip, a flexible and/or movable dividing wall separating the chamber into an unused and a used blister compartment The flexible dividing wall may be fixed to the housing at each end.

In one embodiment, the dividing wall is flexible and configured so that it extends across said space between the sidewalls of the inhaler to prevent passage of powdered dose between the unused and used blister compartments.

Preferably, the width of the dividing wall is greater than the distance between the sidewalls so that the flexible dividing wall is held in compression between the sidewalls so as to prevent passage of powder between the two regions of the chamber around the edges of the dividing wall and the walls of the chamber.

The flexible dividing wall preferably comprises a foam strip.

In one embodiment, the inhalation device comprises a second spiral wound element to receive an unused blister strip prior to insertion of the strip into the housing such that the second spiral wound element retracts as the first spiral wound element expands as the size of the coil formed from a used portion of the strip increases and the size of the coil formed from an unused portion of the strip decreases.

Preferably, the spiral wound element is configured so that it is partially unrolled or unwound by the leading edge of a used portion of a blister strip on initial contact of the leading edge of the strip against the spiral wound element, prior to any substantial deformation of the strip caused by the spiral wound element.

According to the invention, there is also provided a method of controlling a strip of blisters within an inhalation device in which unused blisters are sequentially movable into alignment with means for opening a blister to enable a user to inhale a dose, the method including the step of feeding a used portion of the strip into a spiral wound element to coil said used portion of the strip.

According to the invention, there is also provided a method of forming a coiled strip of blisters for insertion into an inhalation device, the method including the steps of feeding an end of the strip of blisters into a spiral wound element such that the strip is coiled within said spiral wound element.

According to another aspect of the invention, there is provided an inhaler comprising a housing to receive a strip of blisters each containing a dose of medicament and means to sequentially move each blister into alignment with means for opening a blister to enable a user to inhale said dose, the housing including a chamber to receive used blisters and means to compress, crush, tear, cut-up and/or fold said used blisters.

It will be appreciated that different aspects of the invention may be used independently or in any combination with other aspects of the invention. For example, the spiral wound element can be used in conjunction with the flexible wall and/or a device to crush used blisters.

It will be appreciated that the inhaler of the invention may be either a passive or active device. In a passive device, the dose is entrained in a flow of air caused when the user inhales through the mouthpiece. However, in an active device, the inhaler would include means for generating a pressurized flow of gas or air through the blister to entrain the dose and carry it out of the blister through the mouthpiece and into the user's airway. In one embodiment, the inhaler may be provided with a source of pressurized gas or air within the housing.

Embodiments of the invention will now be described, by way of example only, with reference to FIGS. 4 to 20 of the accompanying drawings, in which:

FIGS. 1a and 1b are side sectional views of a conventional inhalation device to show how the blisters of a strip are sequentially moved into alignment with a blister piercing station by movement of an actuator from the position shown in FIG. 1a to the position shown in FIG. 1b which drives an indexing wheel. A piercing head on the actuator pierces the lid of an aligned blister when the actuator is returned to its normal position as shown in FIG. 1a.

Figure 14:
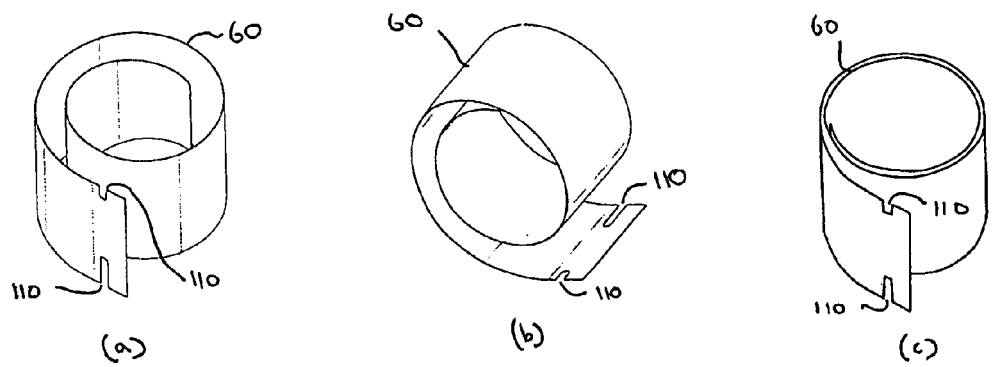
Figure 17:
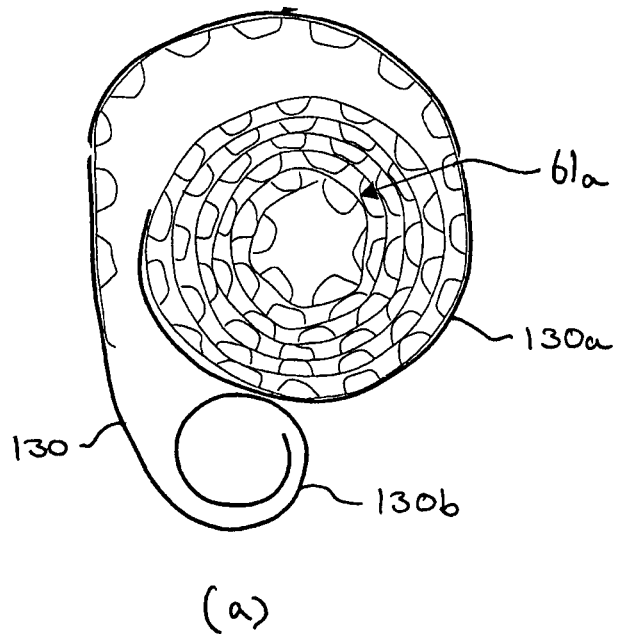
Figure 17:
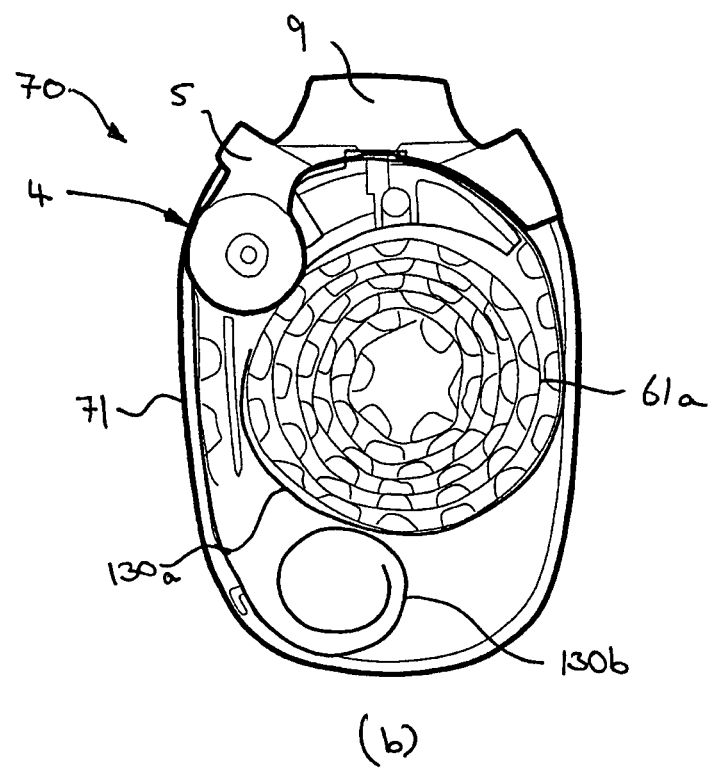
Figure 18:
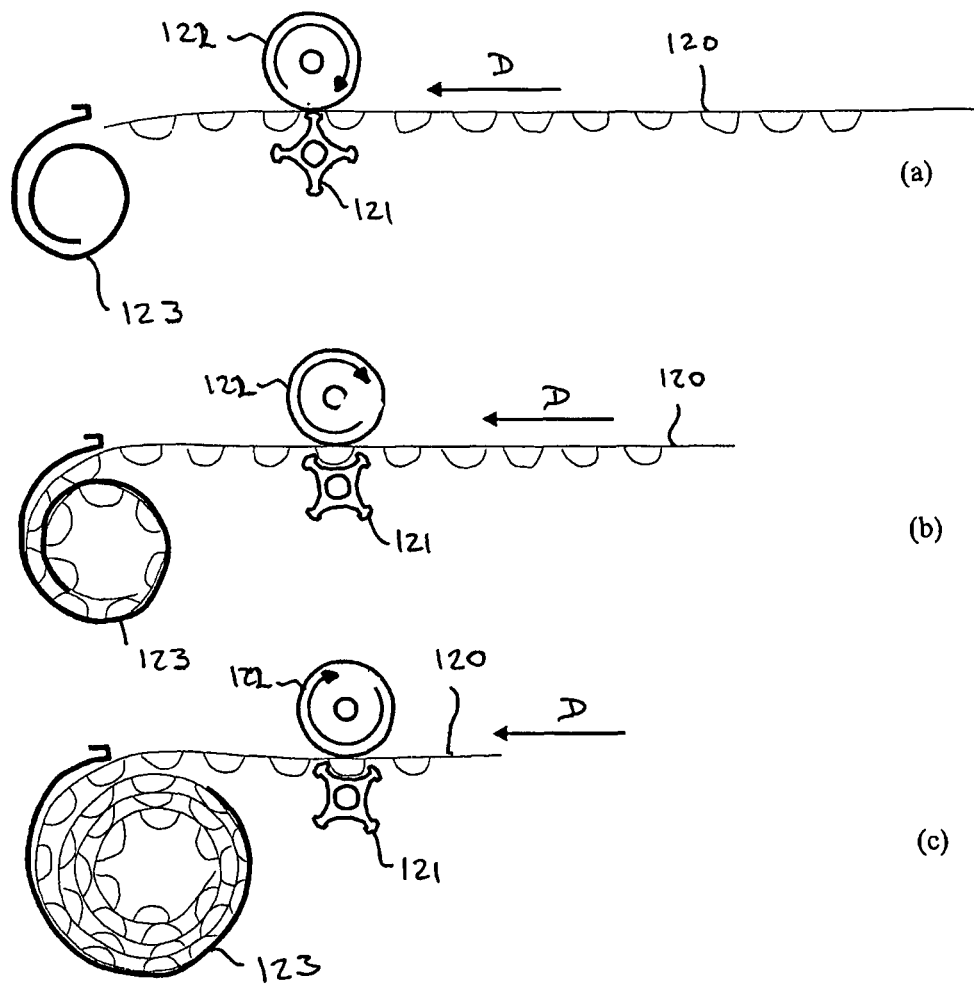
Figure 19:
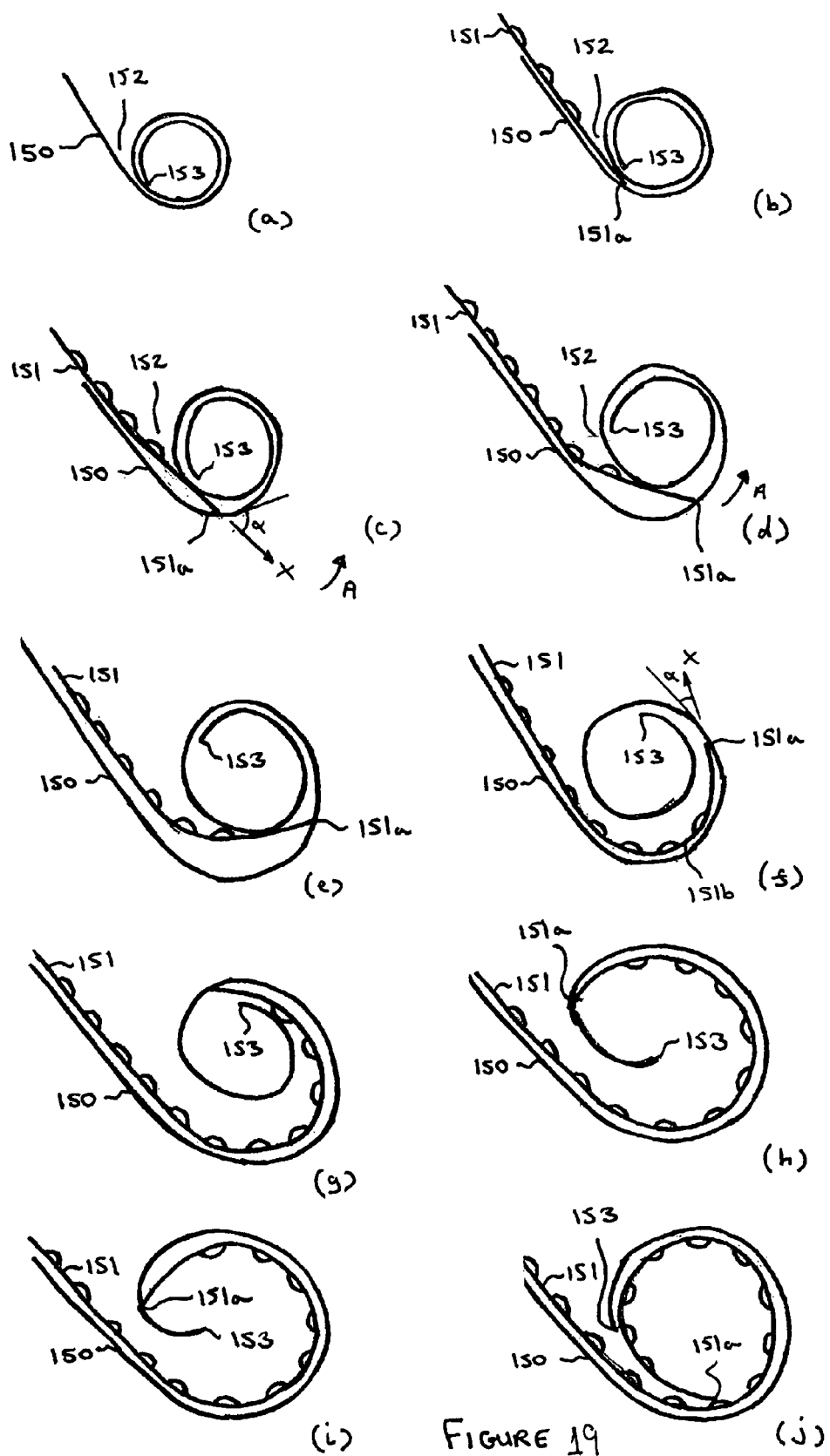
Figure 20:
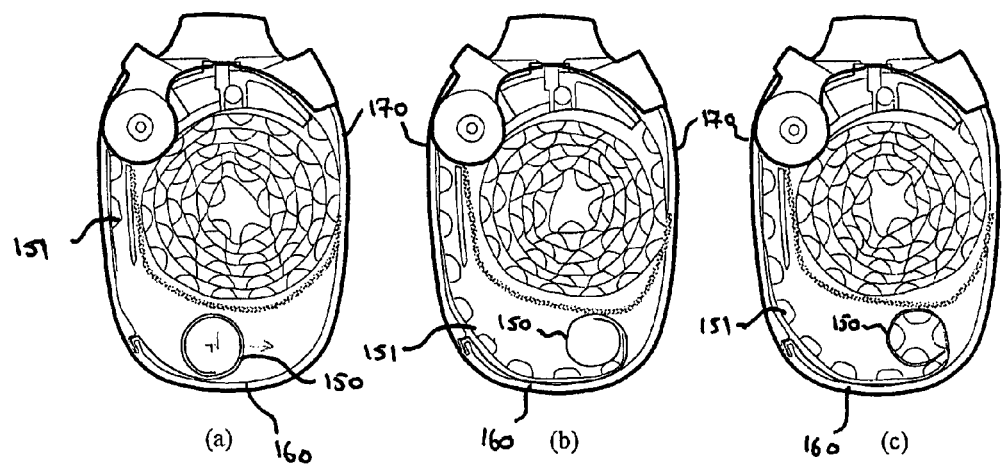
Figure 20:
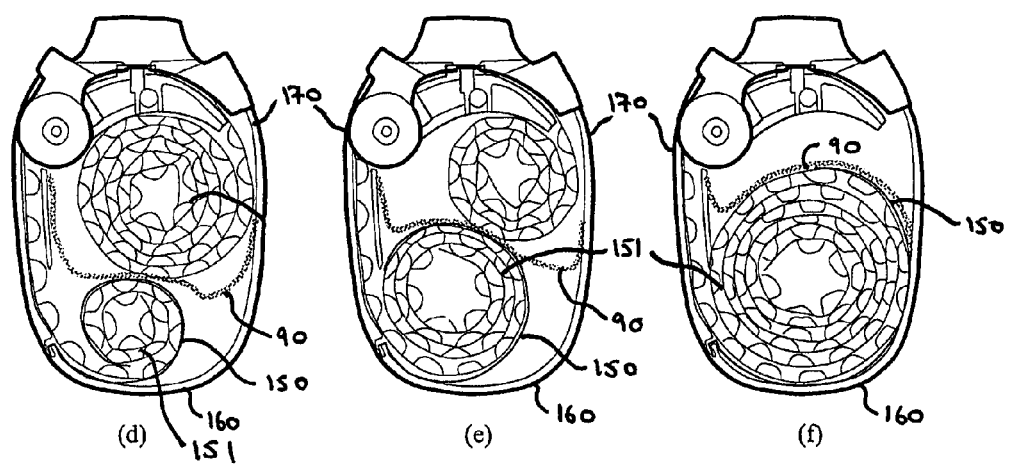
Figure 21:
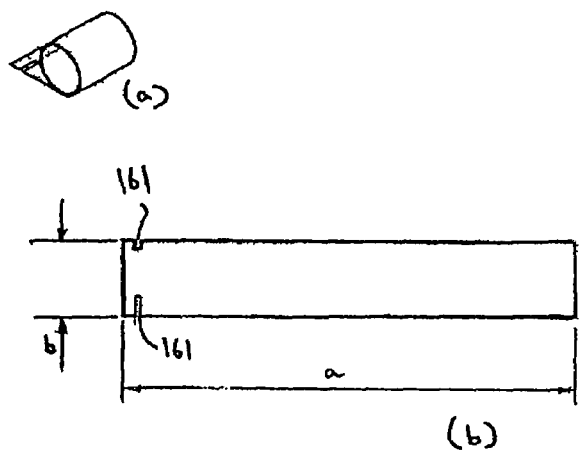
Figure 21:
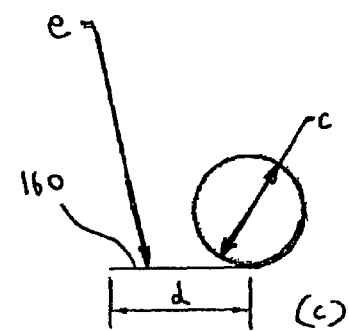

FIGS. 13a and 13b show a modified version of the inhalation device illustrated in FIG. 11a and in which the flexible dividing wall surrounds, and is at least partially attached to, the outer surface of the spiral wound element. In FIG. 13a, none of the blisters have been used and so the spiral wound element is empty. However, in FIG. 13b, all the blisters have been used and the spiral wound element has expanded to its maximum extent together with the flexible dividing wall;

FIGS. 14a, 14b and 14c show three perspective views of a spiral wound element which have notches close to its outer end for attachment to the internal wall of the housing of an inhaler;

FIGS. 15a and 15b show two perspective views of a moulded spiral wound element;

FIGS. 16a and 16b shows a spiral wound element formed from a wire or from a material having a rectangular section, respectively;

FIGS. 17a and 17b show a twin spiral wound element prior to and after insertion into an inhalation device, respectively;

FIG. 18a to 18c show a sequence of drawings to illustrate how a fresh strip of unused blisters may be coiled within a spiral wound element prior to insertion into the housing of an inhalation device;

FIG. 19(a) to 19(j) are a sequence of drawings to show how a coil of used portion of a blister strip is formed in a spiral wound element according to another embodiment;

FIG. 20(a) to 20(f) show how a coil of a used portion of a blister strip is formed with the spiral wound element of FIG. 18 when located in an inhalation device, and FIG. 21(a) to 21(c) shows a perspective view, an unrolled plan view and, a side view of the more flexible spiral wound element shown in FIGS. 19 and 20.

Reference is made throughout this specification to both "unused" and "used" blisters. It will be appreciated that "unused" blisters refer to those blisters that have not passed the blister piercing station and which remain intact with the dose contained therein. "Used" blisters refer to those blisters which have passed the blister piercing station in response to movement of the actuator by a user and which have been pierced to enable access to the dose contained therein to be obtained. Although in general, a "used" blister refers to a blister from which a dose has been inhaled, it should also be taken to include blisters which have passed the blister piercing station and have been pierced but which still contain either some or all of the dose contained therein. This may happen, for example, when a user moves the actuator to move the blister strip without inhaling the dose from a previously pierced blister.

An alternative to both the conventional approach of spooling used blisters, and the loop drive described above, is to employ a mechanism to impart folds to a used strip so that it is encouraged to form a concertina. The device can, alternatively or in addition to a folding mechanism, also include means for crushing the used blister cavities so as to reduce their volume and so that a compacted stack of used blisters is formed, thereby minimizing the volume of space occupied by the used blisters.

Figure 4:
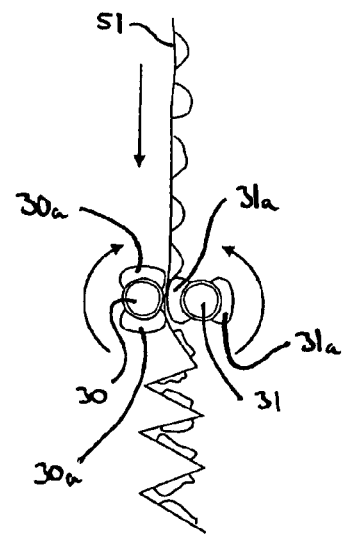
FIGS. 4a to 4c shows an embodiment according to one aspect of the invention in which the used portion of a strip of blisters are folded in a zig-zag or concertina fashion and the blister cavities are crushed so that the used blisters form a neat stack within an enclosed chamber in the housing of the device.
Figure 4:
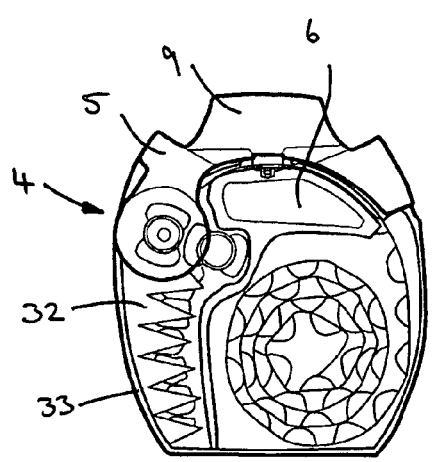
Figure 4:
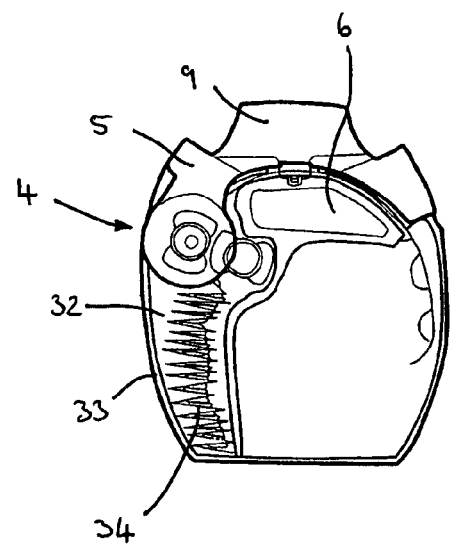

One way in which the concertina folds and crushing of the used blister cavities can be carried out is shown in FIGS. 4a to 4c, from which it can be seen that two lobed rollers 30,31 are configured so as to intermesh with a small gap between them which is less than the depth of a blister cavity. The lobed rollers 30,31 may be connected by integral toothed gear wheels (not shown) so that both are driven, possibly in response to movement of the actuator 5. As a used blister strip 51 passes between the lobed rollers 30,31, the lobes 30a, 31a produce a zig-zag or fold in alternate directions into the flattened strip so as to form a concertina. Each roller has the same construction but they are mounted so the lobes 30a on one roller are 90 degrees out of phase with the lobes 31a on the other roller so that, as the rollers 30,31 rotate, the lobes 30a,31a on one roller 30,31 engage the strip and press it against the other roller between the lobes 30,31a of that roller 30,31. As shown in FIGS. 4b and 4c, if the concertina is forced into an enclosed space 32 within the housing 33 of the inhaler, a compacted stack 34 (see FIG. 4(c)) of used blisters is created. The enclosed space 32 may be provided with a wall or piston (not shown) slidable against a bias provided by a spring (not shown) in response to pressure applied thereto by the used blisters 51 entering the enclosed space 32, so as to minimize the volume occupied by the blisters 51 and maintain the concertina form.

It will also be appreciated that, in place of the lobes 30a, 31a, one or both of the rollers 30,31 may be provided with an arm having a cutting blade (not shown) affixed to its tip so that rather than fold the strip, the cutting blade engages the strip 51 to cut it or chop it up into sections or individual blisters.

Figure 5A:
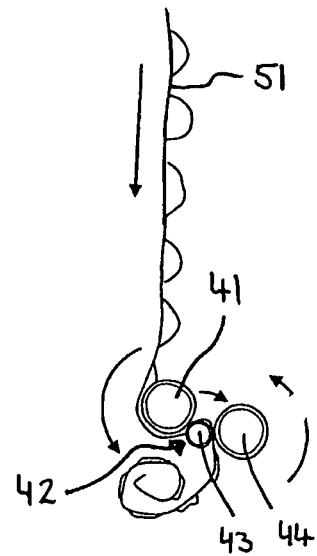
FIGS. 5a and 5b show another embodiment according to one aspect of the invention in which the used portion of the blister strip is driven through a nip between at least one pair of rollers to crush the blister cavities and impart a curvature to the strip so that it coils up within an enclosed chamber in the housing of the device.
Figure 5B:
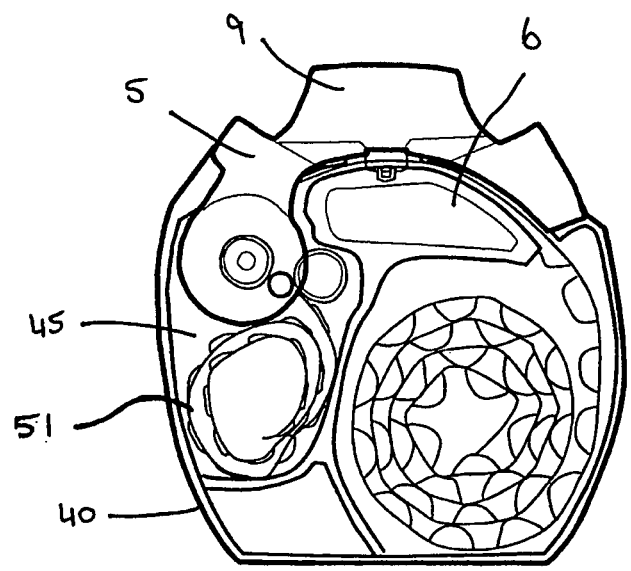

In another modification, illustrated in FIGS. 5a and 5b, the blister cavities of the used blister strip 51 can simply be crushed without imparting any fold to the strip 51. If the strip 51 is passed around a roller 41 and through a nip 42 between that roller 41 and at least one other roller 43, 44, the rollers 41,43,44 will crush the cavities and will also tend to form a curvature in the strip 51 such that a coil is formed which can be directed into an enclosed space 45 within the housing 40, as shown in FIG. 5b.

It will be appreciated that techniques other than rollers can be used to crush or flatten the blisters in order to reduce their size. They may be compressed between moving parts, or between a moving part and an anvil. The moving part may be driven by the actuator or by separate means. The blister form may be weakened in manufacture to reduce the force needed to crush the blister, for example by scoring the blister form.

In one unillustrated embodiment, the indexing wheel forming part of the indexing mechanism and which rotates to draw the blister strip through the device past the piercing station may be itself be used to squeeze the used blister cavities as they pass around it, thereby at least partially crushing them. This is achieved by enlarging the axle or hub of the indexing wheel so that the distance between the hub and the casing of the device, or a component fixed to the casing, is less than the maximum height of a blister cavity. As the blister cavities are entrained between the spokes of the indexing wheel, onward rotation of the wheel causes the cavities to be at least partially squashed or sandwiched between the enlarged hub of the indexing wheel and the casing of the device.

Figure 5C:
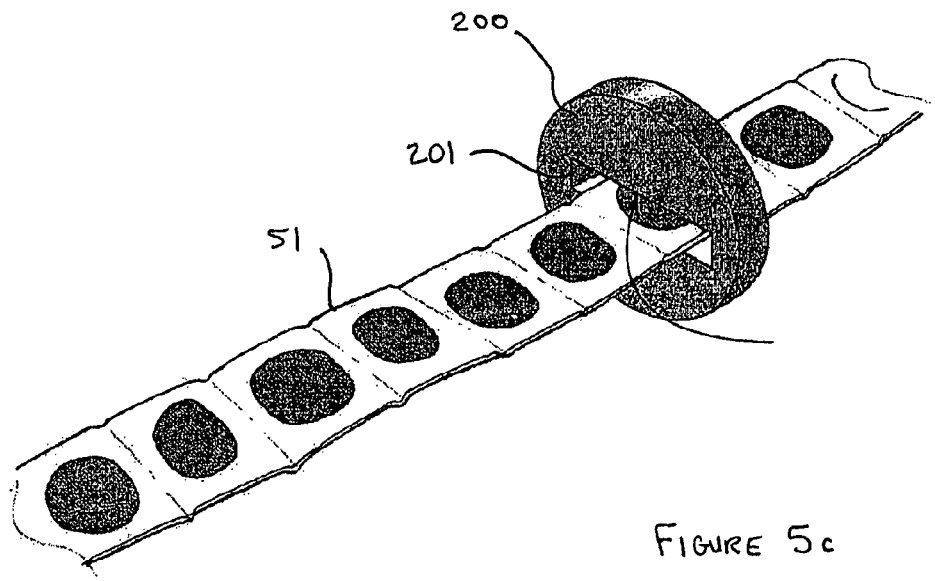
FIGS. 5c and 5d shows a simplified embodiment of a mechanism for tearing or otherwise detaching used blisters, which may have been crushed, from remaining blisters.
Figure 5D:
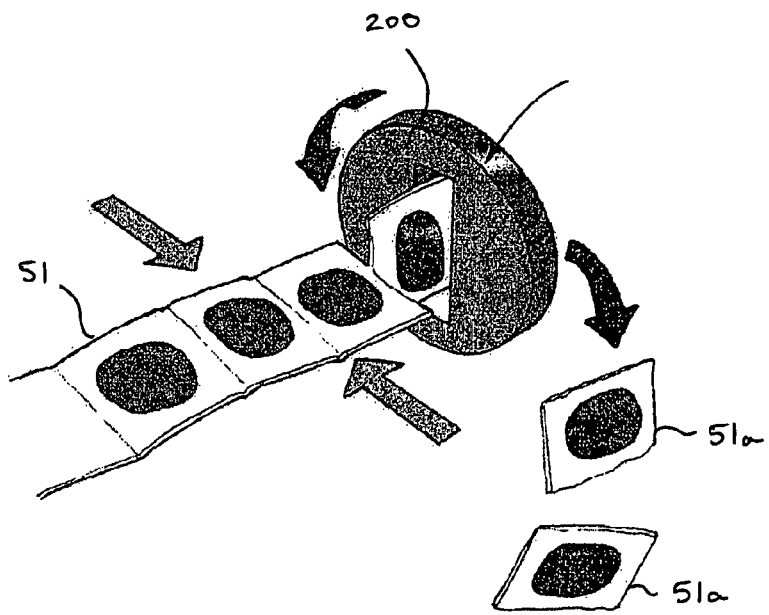

In FIGS. 5c and 5d, a mechanism for tearing or separating a used blister 51a from the strip 51 is shown. The used blisters may or may not have been crushed prior to being separated. As can be seen from FIG. 5a, the strip 51 passes through a "letterbox" shaped opening 201 in a rotatably mounted tearing wheel 200. Means (not shown) are provided to keep the strip in a fixed position upstream from the point at which it passes through the tearing wheel 200 so that, when the tearing wheel 200 rotates a section of the strip 51 is torn off. The tearing wheel 200 may be driven by gear wheels that rotate in response to movement of the actuator 5. The detached blisters 51a are allowed to fall into a containment section or enclosed space within the housing 2.

Figure 6:
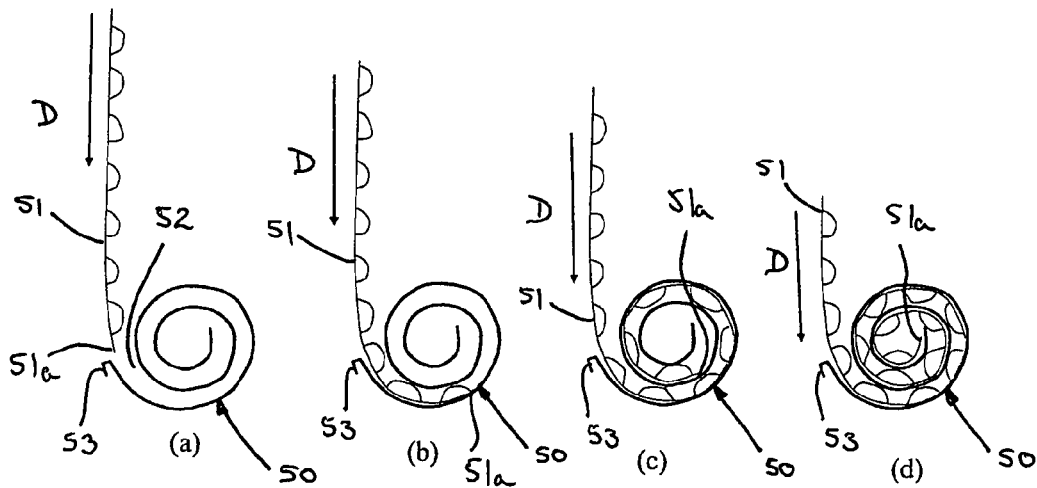
FIG. 6a to 6d shows a sequence of drawings to show how the used portion of the blister strip may be fed into a rigid spiral wound element so as to cause the used portion of the strip to coil up as it is guided by the surface of the spiral wound element, according to an embodiment of the invention.

Referring now to FIG. 6, there is shown a rigid spiral wound element 50 and a used portion of a strip of blisters 51. As the used portion of the strip of blisters 51 sequentially move through the device in response to successive actuation of an indexing mechanism by the user, the used portion of the strip 51 moves in the direction of arrow "D" as the size of the used portion of the blister strip gradually increases. As shown in FIG. 6(a), the leading end 51a of the used portion of the strip is about to enter the mouth 52 of the spiral wound element 50. In FIG. 6(b), the used portion of the strip 51 has entered the mouth 52 and has been deflected by the surface of the spiral wound element 50 so that it begins to follow a curved path guided by the surface of the spiral wound element 50. In FIG. 6(c), the used portion of the strip 51 has passed further into the spiral wound element 50 so as to form a complete coil. Further movement of the used portion of the strip 51 into the spiral wound element 50 results in the formation of multiple coils from the used portion of the blister strip, as shown in FIG. 6(d). As the spiral wound element 50 is rigid, no more blisters can be received within the spiral wound element when the leading end 51a of the used portion of the blister strip 51 reaches the centre of the spiral, as shown in FIG. 6(d).

Figure 7:
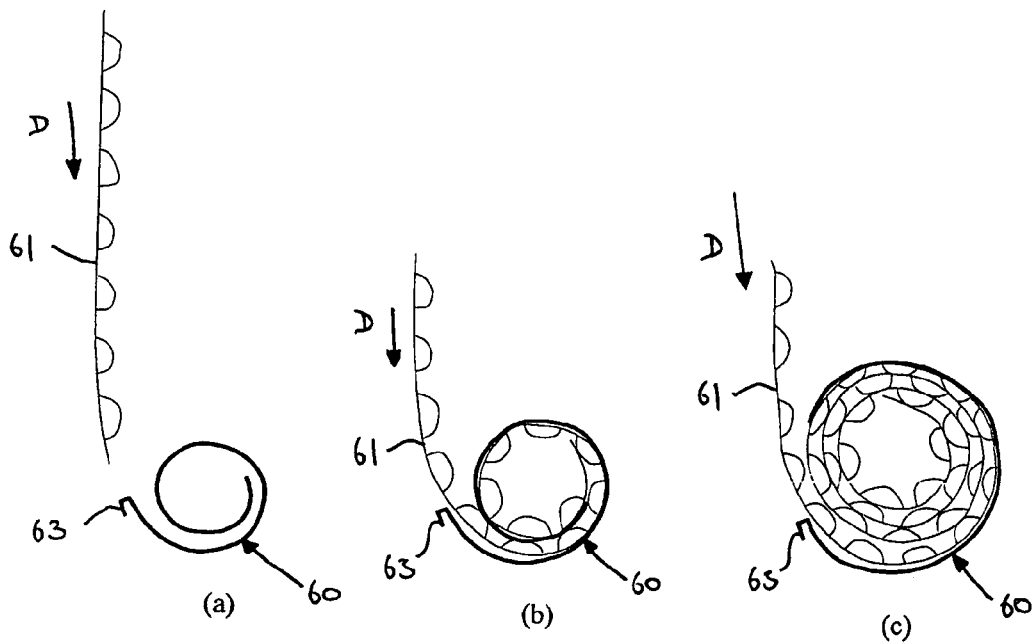
FIG. 7a to 7c shows a sequence of drawings to show how the used portion of the blister strip may be fed into a flexible spiral wound element that expands as the used portion of the coiled blister strip grows within it, according to an embodiment of the invention.

It will be appreciated that when the leading end 51a of the used portion of the strip 51 reaches the centre of the spiral, no more can be inserted as the spiral wound element 50 shown in FIG. 6 is rigid. Therefore, in a more preferable configuration, the spiral wound element 60 is formed from a flexible, preferably resilient, material so that it expands as the number of coils of used blisters 61 increase, as shown in the sequence of drawings of FIG. 7. Once a coil of blisters 61 has been formed within the spiral wound element 60, further movement of the used portion of the strip 61 into the spiral wound element 60 causes it to expand as the coiled used portion of the blister strip 61 grows, as shown in FIG. 7c. The initial size and rigidity of the spiral wound element 60 may be selected in dependence on the stiffness of the used portion of the blister strip 61 such that, as the used portion of the strip 61 is received in the spiral wound element 60, it is guided by the spiral wound element 60 until it forms a first closed coil, as shown in FIG. 7b. Only once this first closed coil has been formed does any expansion of the spiral wound element 60 take place. In practice, a blister strip 61 consisting of 16, 30 or 60 or more blisters can be successfully formed into a coil in this way. It will of course be appreciated that there may be some initial expansion of the spiral wound element 60 during formation of the first closed coil.

In both versions of the spiral wound element shown in FIGS. 6 and 7, the outer end of the spiral has a hook 53, 63 to facilitate the attachment of the spiral wound element 50, 60 to a suitable formation on the inner wall of a housing of a device. Other means of providing corresponding locating features to secure the element may be used. FIGS. 14(a), (b) and (c) show a spiral wound element 60 with notches 110 formed in it close to its outer end for location on corresponding formations on the housing.

Although the blister strip 51, 61, in the embodiments of FIGS. 6 and 7, is shown coiling up within the spiral wound element 50, 60 with the pierced upper surface of the blister strip facing outward, i.e. facing the surface of the spiral wound element 51, 61, it will also be appreciated that the blister strip can be encouraged to coil with the pierced upper surface facing the centre of the spiral wound element. In this way, the strip itself serves as a flexible wall to prevent the passage of residual powder around the strip. To assist in this, the blister strip can be made slightly wider than the distance between the walls of the device and more flexible so that it constantly engages with the walls of the device with sufficient force to prevent the passage of residual powder around the strip but still enabling coiling and indexing of the strip. The coil thereby effectively becomes a self-sealing enclosure preventing escape of residual powder out of the coil.

Figure 8:
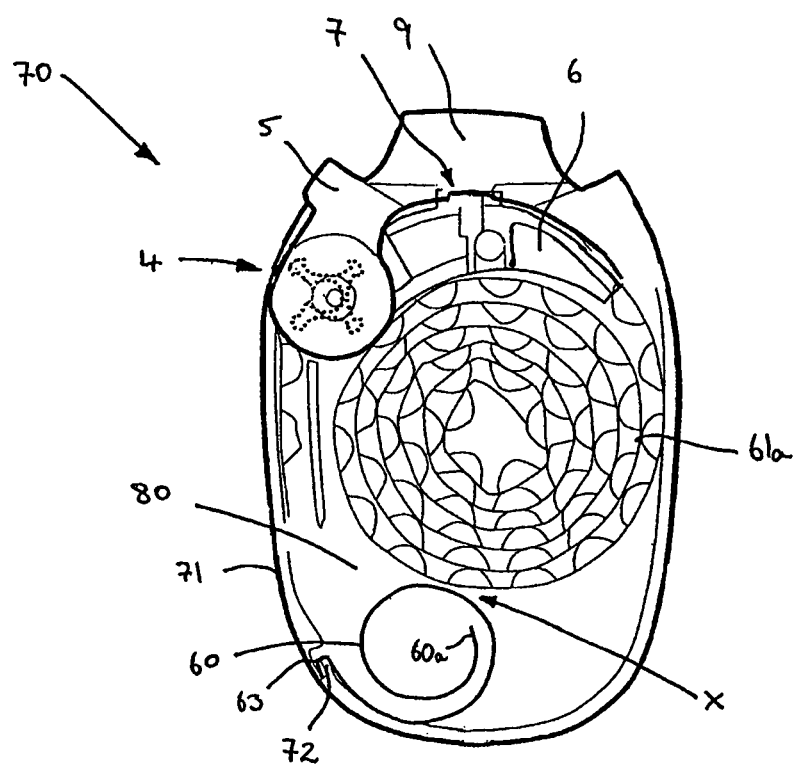
FIG. 8 shows an embodiment of an inhalation device incorporating a coil such as that shown in FIG. 7.
Figure 9:
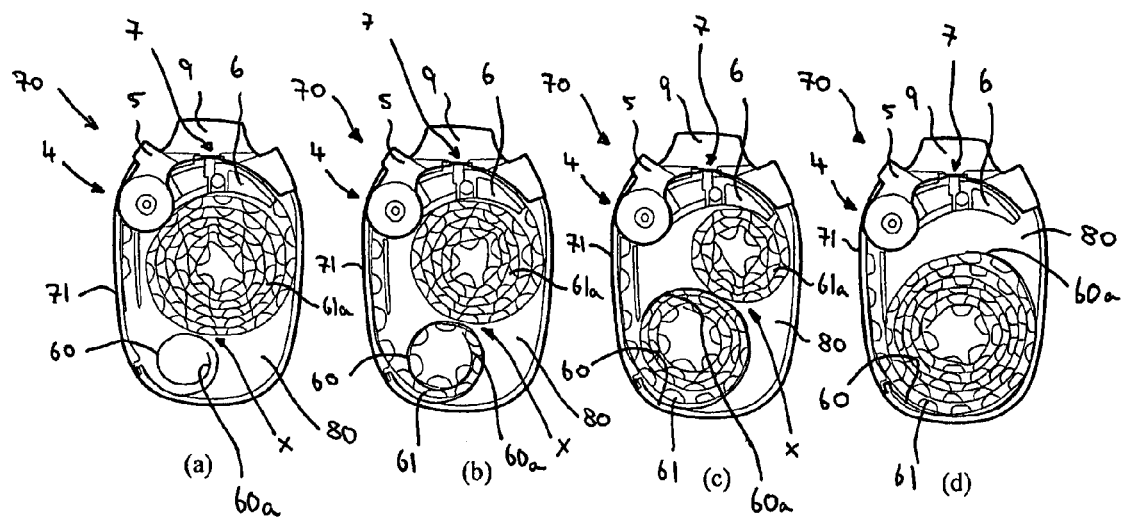
FIG. 9a to 9d shows a sequence of drawings to show how the unused portion of a coiled strip of blisters gradually unwinds as the blisters pass the blister piercing station and the used portion of the blister strip is coiled up within the spiral wound element.
FIG. 9e shows an embodiment similar to that shown in FIG. 8 but in which a blocking element is secured to the end of the blister strip.

An embodiment of an inhalation device 70 incorporating a spiral wound element 60 to form a coil from a used portion of a blister strip 61 in the way described with reference to FIG. 7 is illustrated in FIGS. 8 and 9. It will be appreciated that the general construction and operation of the device shown in FIG. 8 is similar to that of the device shown in FIGS. 1a and 1b, except that the used part of the blister strip 61 is retained within the device 70 and formed into a coil by a spiral wound element 60 located within the housing 71 of the device, rather than being ejected from it. Accordingly, the indexing mechanism 4 pushes the used portion of the strip 61 into the spiral wound element 60 as well as drawing the unused portion of the strip 61a from the starting coil over the blister location chassis 6 and past the blister piercing station 7. The indexing mechanism 4 moves the strip 61 incrementally one blister at a time, i.e. activation of the indexing mechanism sequentially moves a blister into alignment with the blister piercing station so that access to the contents of each blister may be obtained one by one.

As can be seen most clearly from FIG. 8, the hook 63 on the spiral wound element 60 hooks over a protrusion 72 formed within the wall of the housing to attach the spiral wound element 60 thereto.

It will be appreciated that the dimensions of the device shown in FIG. 8 are generally the same as that of the device shown in FIG. 1, except that the housing 71 is elongated by the starting diameter of the spiral wound element 60, which is typically 20 mm or less.

For obvious reasons, it is desirable to ensure that the dimensions of the device are kept within reasonable limits. This enhances patient acceptability and portability of the device. Therefore, the housing has a common chamber 80 within it that receives both unused and used portions of the blister strip. Prior to use of the inhaler 70, a large proportion of the chamber 80 is occupied by the coil of unused blisters 61*a*, the remaining, much smaller portion, being occupied by the spiral wound element 60. As the diameter or size of the unused portion of the strip 61*a* reduces during use, the coil formed from the used portion of the strip 61 increases in diameter causing the spiral wound element 60 to expand and increase in diameter as more and more of the blisters are used and coil up within it. As the size of the coil formed from the used portion of the strip 61 increases, and the spiral wound element 60 expands and grows, it occupies the space previously occupied by the unused portion of the strip of blisters 61*a*. Therefore, the chamber 80 is common to both used 61 and unused 61*a* portions of the strip, as opposed to having a separate chamber for each. Consequently, the overall size of the device 70 can be kept to a minimum.

It is desirable for the coil formed from the used portion 61 of the blister strip in its initial state to occupy as little space as possible and in its final state to occupy as much of the space previously occupied by the unused portion 61*a* of the blister strip as possible. Preferably the unfilled spiral wound element 60 has a diameter less than 50% of the diameter of the coil of the unused portion 61*a* of the blister strip and more preferably less than 40%. In yet further preferred embodiments, the unfilled spiral wound element 60 has a diameter less than 20-40% of the diameter of the coil of the unused portion 61*a* of the blister strip and more preferably still less than 25%. In the embodiment of FIG. 8 it has a diameter of 38% of the diameter of the coil of the unused blisters 61*a*. Preferably the coil of used blisters 61 in its final state occupies greater than 50% of the space previously occupied by the unused portion 61*a* of the blister strip.

It can be advantageous for the outer surface of the spiral wound element 60 to press against or contact the coil formed from the unused portion 61*a* of the blister strip, as generally indicated by arrow "X" in FIGS. 8 and 9, as the unused portion 61*a* of the blister strip reduces in diameter and the used portion 61 of the blister strip increases in diameter. This can assist in steadying the spiral wound element 60 as it expands and also helps maintain a tighter coil formed from the unused portion 61*a* of the blister strip.

The spiral wound element 60 for coiling up the used portion 61 of the blister strip has been found to work with blister strips of varying degrees of thickness. The strip is required to have at least a certain degree of rigidity and stiffness otherwise it cannot withstand the compressive force exerted on it by the indexing mechanism 4 and buckles. Devices with spiral wound elements 60 have been proven to work with blister strips formed from a base layer of either 25 μm nylon/45 μm aluminum/30 μm PVC or 25 μm nylon/45 μm aluminum/60 μm PVC, containing over 60 blisters and over 660 mm in length. Spiral wound springs, such as a coil spring, have been formed from phosphor bronze, stainless steel, nylon, acetal and polypropylene. It will be appreciated that the device 70 will function adequately with a wide range of materials and dimensions for both the blister strip and the spiral wound element 60.

Figure 15:
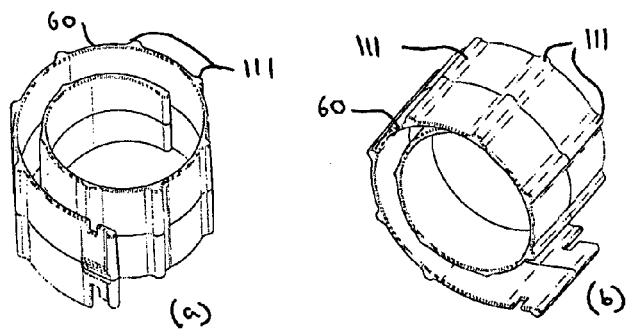
Figure 16:
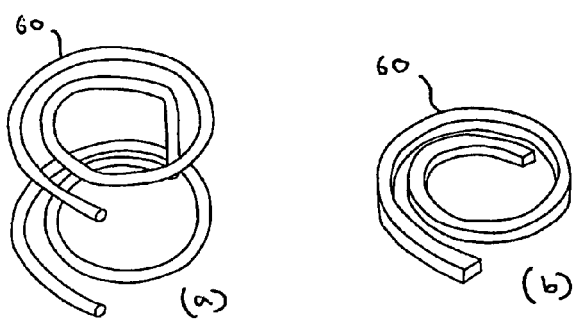

The spiral wound element 60 is generally formed from a thin sheet of material (as shown, for example, in FIGS. 14*a* and 14*b*) or, it can be moulded in the form of a spiral (see FIGS. 15(*a*) and 15(*b*). When moulded, the surface of the element 60 may be provided with raised regions 111 to facilitate ejection of the element from the mould. It can be also be formed from wire or a thicker rectangular section material, as shown in FIGS. 16(*a*) and 16(*b*), so that friction between the blister strip and the surface of the spiral wound element 60 is reduced due to a smaller region of contact between the strip and the element 60. As described earlier a range of materials can be used in the construction of the spiral 60.

Although the spiral wound element 60 preferably has a degree of resilience, it is also envisaged that the spiral wound element 60 could be constructed from a material, such as a polymer, which creeps and relaxes as it expands thereby relieving the load on the wound blister coil. Creep may occur to at least some extent even in a resilient spiral wound element 60 as all polymers are subject to at least some degree of creep.

The spiral wound element 60 preferably has at least one complete spiral or coil extending over an angle that exceeds 360 degrees. However, it will be appreciated that it may also have a plurality of coils or portion of a coil. FIGS. 14*a* and 14*b* show a spiral wound element with one and a half turns, or 540 degrees. The coil in FIG. 14*a* can be formed from stainless steel between 0.8 and 0.15 mm thick, preferably 0.12 mm thick. Such a coil can also be formed from phosphor bronze between 0.1 mm and 0.18 mm thick, preferably 0.15 mm thick. The coil in FIG. 13*c* can be moulded from acetal with a nominal thickness of between 0.3 mm and 1.0 mm, preferably 0.5 mm.

These thicknesses are selected to give a similar stiffness irrespective of the material. Stiffness of a flat spring is proportional to Young's Modulus and the cube of the material thickness. The Young's Moduli of stainless steel, phosphor bronze and acetal are 192, 103 and 3.1 GPa respectively. Hence nominal thicknesses of 0.12, 0.15 and 0.5 mm will give similar stiffness.

Coils with two or more turns can also be used. These perform well with thinner material, for example stainless steel 0.05 mm thick. This will have a stiffness approximately 7% of that of a coil formed from material 0.12 mm thick, and it behaves in a different way, as shown in FIGS. 19 and 20 and as will be explained later. The increased flexibility of the thinner material also allows a smaller coil to be used. In one example used to accommodate a 60 blister coil, a coil of the type shown in FIG. 14*a* with a nominal starting diameter of 20 mm could be replaced by a longer thinner coil with a starting diameter of 12 mm. The more flexible coil has the further advantage that it is more tolerant of friction caused, for example, by waste powder rubbing between the coil and the strip.

In any embodiment that employs a spiral wound element of the type described, the stiffness of the spiral wound element may be constant along its length. However, it can be advantageous to provide the spiral wound element with a region of reduced stiffness towards its inner end 60*a* as this helps the spiral wound element to assume a rounder form as it expands and helps to prevent the end of the spiral wound element from "clawing" against the surface of the blister strip. The stiffness can easily be varied by changing the thickness or width of the spiral wound element or forming it so that it tapers towards its inner end 60*a*. In a preferred arrangement, the spiral wound element tapers for a portion of its length towards the inner end. A 50% reduction in section area over the last 20 mm of the length of the spiral has been found to work well. The spiral wound element can also be provided with a series of holes or slots in it to reduce its stiffness.

It will be appreciated that any embodiment that employs a spiral wound element for coiling up a used portion of a blister strip can also employ means for crushing the blister cavities prior to the used portion of the blister strip being received within the spiral wound element, such as those means described previously.

Figure 9E:
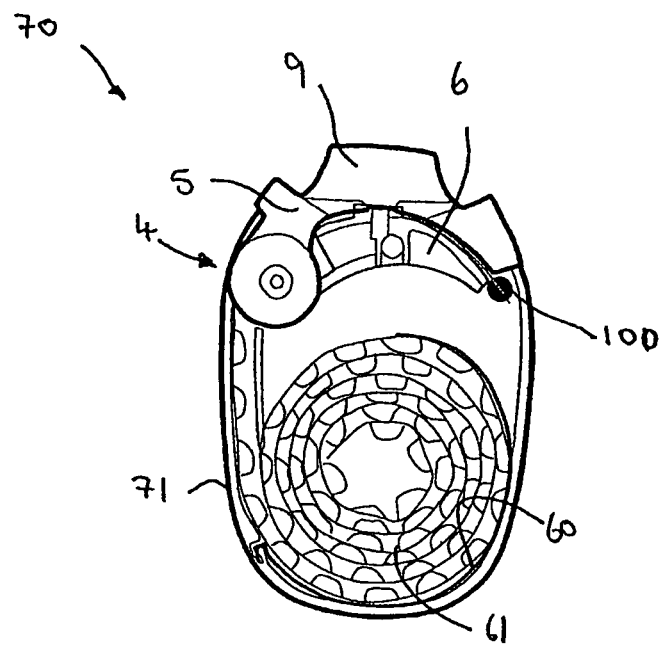

When the end of the strip is reached, it passes through the blister location chassis 6 and indexing mechanism 4. However, it may be desirable to implement a blocking feature so that repeated actuation of the device when the blister strip has been exhausted is prevented. This would clearly indicate to the patient that all doses have been taken. The blocking feature may take the form of an enlargement attached to or formed from the end of the strip that is physically too large to pass through the blister location chassis 6. For example, as illustrated in FIG. 9e, a cylindrical or spherical plastic moulding 100 is securely clipped to the end of the blister strip during assembly. The moulding 100 has no effect on the operation of the device until the end of the strip reaches the blister location chassis 6, where further movement of the strip and actuator 5 is prevented. It will be appreciated that many other methods of creating a blocking element on the end of the strip could be used, including various shapes of plastic moulding or by forming and/or folding the end of the strip itself. However, it will be appreciated that a blocking element is not essential and, once all the blisters of a strip have been used, continued operation of the indexing mechanism will result in almost the entire length of the strip being coiled within the spiral wound element, the used portion of the strip will then comprise all the blisters of that strip.

Although the housing of an inhalation device may be provided with a common chamber 80 that stores the unused portion of the blister strip 61a, powder contamination of the unused portion 61 of the blister strip needs to be addressed for reasons that have already been described.

The aforementioned problem is at least partially addressed by the provision of the spiral wound element 60 because the opening in at least some of the used blister cavities lies against the inner surface of the element 60, thereby preventing escape of residual powder from the blister cavities. It is also envisaged that the edges of the spiral wound element 60 may be provided with sealing elements, such as plastic strips formed in a U-shape to create lip seals, brushes or wipers, where they contact adjacent walls of the chamber to assist in retaining residual powder that does escape from the blister cavities within the coils of the spiral wound element 60. As long as the sealing elements are thin and flexible, the strip can seal between the inner surfaces of the housing without impeding expansion of the spiral wound element 60.

In another alternative arrangement, a spiral wound element 60 may be lined with a flexible tape that overlaps the edges of the element so as to create a wiper seal against the surfaces of the device walls. However, the sealing effect provided by the spiral wound element 60 itself may not alone be sufficient to prevent powder contamination of the unused portion of the blister strip 61a. Furthermore, to provide a complete barrier around the used portion of the blister strip 61 requires a longer spiral wound element 60 because, as the spiral wound element expands, a section of the spent coil and its associated cavities becomes exposed.

To at least partially overcome the problem of contamination of unused blisters with residual powdered dose, the Applicant's have proposed the provision of a flexible, or inflexible but movable, dividing wall so as to separate the interior of the housing into a unused blister chamber and, a used blister chamber. This wall constrains any residual powder within the used blister portion of the housing.

To reduce the size of an inhalation device, the Applicants have proposed allowing the space initially occupied by the unused portion 61a of the blister strip to be being slowly taken up by the used portion 61 of the blister strip as the size of the used portion 61 of the blister strip increases and the size of the unused portion 61a of the blister strip decreases. To address the problem of powder contamination, a flexible and/or movable dividing wall 90 is interposed between the unused portion 61a of the blister strip and the part of the housing 71 that receives the used portion 61 of the blister strip so as to divide the chamber 80 into "clean" and "contaminated" regions containing the unused blisters 61a and the used blisters 61, respectively.

It will be appreciated that a flexible and/or movable dividing wall 90 can be used in an inhaler 70 with, or without, the spiral wound element 60 described previously, although particular benefits have been obtained as a result of using both a flexible dividing wall 90 and a spiral wound element 60 in combination as the interaction between these components has some advantages, as will become apparent from the following description.

In one unillustrated embodiment, the dividing wall may simply be a rigid element which is fixed at one end so that it can pivot about this point. Alternatively, it can be slideably fixed to the housing so that it slides depending on the relative size of the unused and used blister strips. However, in a preferred embodiment, and as shown in FIGS. 10 to 13, the dividing wall 90 is flexible and resilient in nature and has one or both ends immovably fixed in place within the housing 71 of the device. It is also envisaged that a flexible dividing wall 90 may be elastomeric in nature so that it can expand and lengthen as pressure is applied to it by an expanding spiral wound element 60 or used blister coil 61.

Although the flexibility of the dividing wall 90 may be such as to allow the relative sizes of the unused and used blister strip compartments to change as the device is used, the flexibility also improves or assists in the sealing of the edges of the dividing wall 90 against the walls 2a,2b of the device housing 71 against which they rub. The width of the dividing wall 90 may be greater than the width of the space, defining the unused and used blister chamber, between the side walls 2a,2b so that the dividing wall 90 is always held in compression between the sidewalls 2a,2b in a direction extending across its width so as to maintain the edges of the dividing wall 90 in close contact with the sidewalls 2a,2b of the housing, thereby minimizing egress of powder from the used blister strip compartment into the unused blister compartment between the edges of the dividing wall 90 and the sidewalls 2a,2b of the housing 71 against which they are held in contact. It is also possible to provide the edges of the dividing wall 90 with sealing elements (not shown), such as plastic strips formed in a U-shape to create lip seals, brushes or wipers, where they contact adjacent walls 2a,2b of the housing 71 to assist in retaining residual powder that does escape from the blister cavities within the contaminated compartment of the housing 71.

Figure 10:
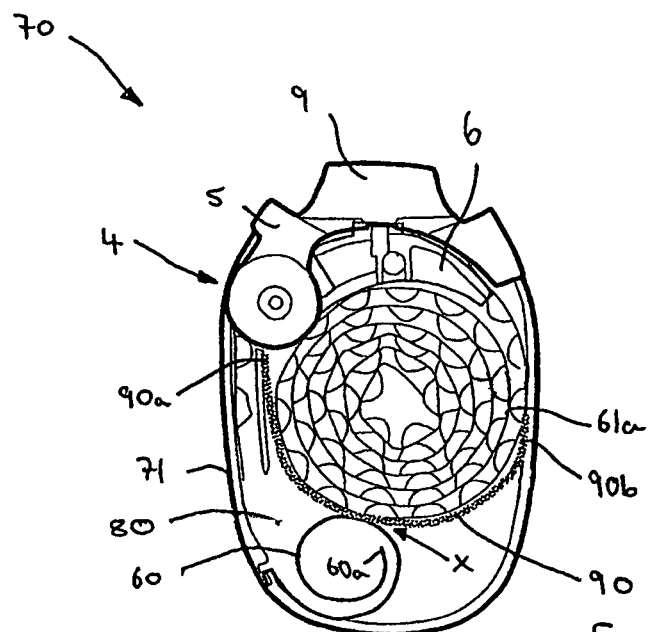
FIG. 10 shows an embodiment of an inhalation device having a housing defining an interior chamber containing a coiled, unused strip of blisters and a spiral wound element to receive a used portion of that blister strip, the chamber is divided into two between the unused blisters and the spiral wound element by a flexible dividing wall to form an unused and a used blister compartment.
Figure 11:
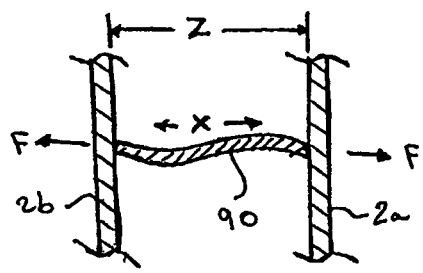
FIG. 11 shows a partial side sectional view across the housing to illustrate how the flexible dividing wall is held in compression between the sidewalls of the housing.
Figure 12:
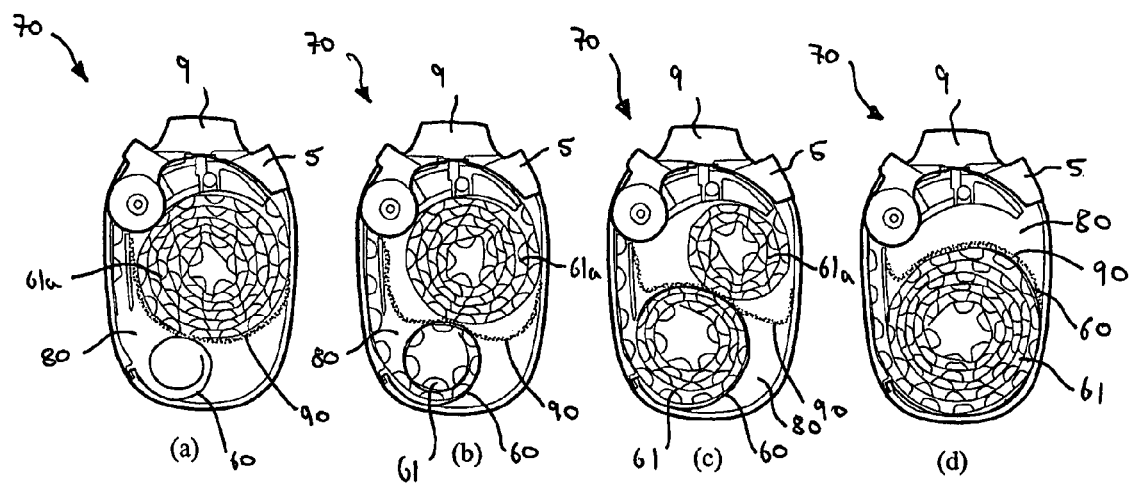
FIG. 12a to 12d shows a sequence of drawings to shown how the flexible dividing wall moves as the spiral wound element expands as it fills up with used portion of the blister strip.

FIG. 10 illustrates an embodiment of the invention in which a flexible movable dividing wall 90 extends over the spiral wound element 60 and separates the used portion 61 of the blister strip from the unused portion 61a from each other. The dividing wall 90 is fixed at each end 90a,90b to the walls of the device. FIG. 11 illustrates a partial sectional view to illustrate how the dividing wall 90 is resiliently flexible in a direction across its width "X" and is wider than the distance "Z" between the two facing sidewalls 2a,2b of the housing 2, so that the dividing wall 90 is slightly deformed and held in compression between the two sidewalls 2a,2b in a direction across its width so that the edges of the dividing wall 90 apply pressure to the sidewalls 2a,2b in the direction indicated by "F" in FIG. 11. Although the pressure applied to the sidewalls 2a,2b by the dividing wall 90 needs to be sufficient to prevent escape of powder from the used blister compartment to the unused blister compartment, it is important to ensure that the pressure is not so great that the friction between the dividing wall 90 and the side walls 2a,2b is too great so as to disrupt or prevent fluid movement of the dividing wall 90 as the used blister strip 61 or spiral wound element 60 expands and pushes against it.

FIGS. 12a to 12d show how the flexible dividing wall 90 is moved or resiliently deformed by a strip of used blisters or, the expanding spiral wound element 60, during the life of the device 70 and as the unused portion 61a of the blister strip unwinds and the used portion 61 of the blister strip winds up within the spiral wound element 60 or is otherwise contained within the used blister compartment.

In one embodiment, the flexible dividing wall 90 can be formed from a flexible foam strip which is dimensioned so that it is lightly compressed between the front and rear housing walls so that an effective powder seal is maintained even as the foam strip is moved by pressure applied to it by the expanding spiral wound element 60. Foam provides a good balance between flexibility and low frictional resistance. Foams can be produced from EVA, PVA, PU and silicone, although it will be appreciated that many other materials could be used instead.

Depending on the stiffness of the foam strip, a stiffening strip (not shown), narrower than the foam strip, may be fixed to the foam strip to increase stiffness. Alternatively, a strip formed of linked rigid sections can be fixed to the flexible sealing strip to control its movement. In another unillustrated embodiment, the dividing wall 90 may itself be formed from a chain of individually rigid segments pivotally linked to each other.

Figure 13:
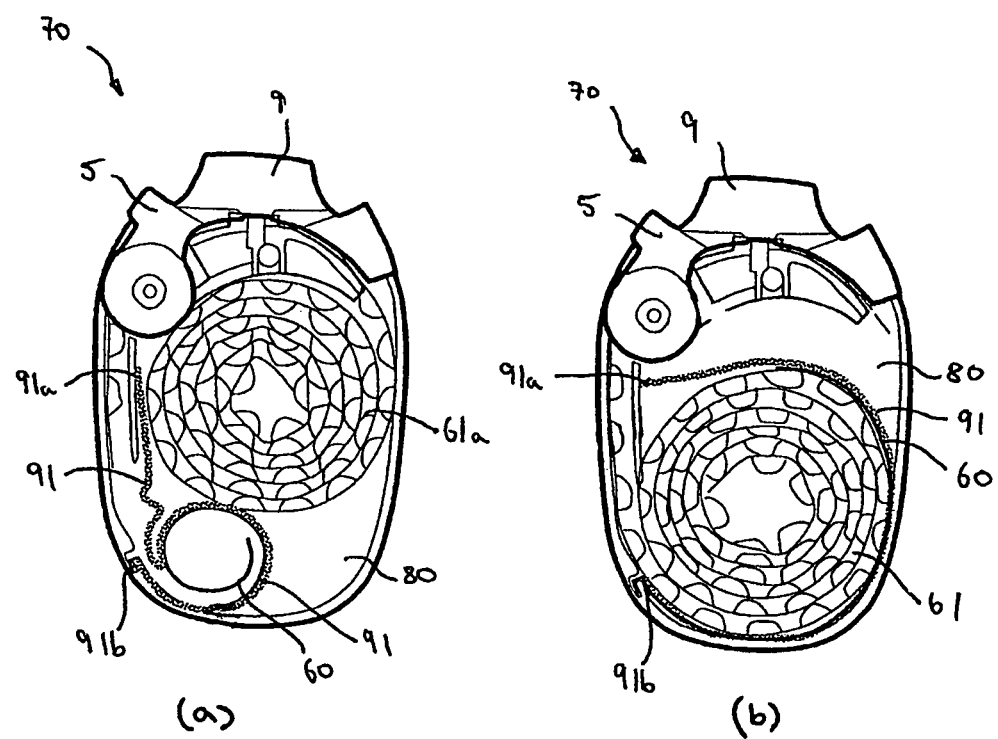

In another modified arrangement, a flexible dividing wall 91 or a portion of it can be at least partially fixed to the outer surface of the spiral wound element 60, as shown in FIG. 13. As with the embodiment of FIG. 12, at least one end of the dividing wall 91a,b can be fixed to the walls of the device.

The provision of a spiral wound element 60 having a stiffness which is sufficient to ensure that there is little or no expansion until a first closed coil of a used portion of the blister strip is formed has proved to successfully control the coiling and storage of the used portion of the blister strip within the device. However, it has been found that in circumstances where a relatively large amount of residual drug remains within the device, such as may occur when a blister is pierced but the dose is not inhaled prior to indexing to the next blister, it can find its way between the used portion 61 of the blister strip and the surface of the spiral wound element 60 which can result in an increase in friction between these components and ultimately cause the used portion 61 of the blister strip to jam within the coil 60. The extent to which this may occur depends not only on the amount of residual drug but also on the type of drug itself and the particle size.

With the aim of minimizing the occurrence of jamming, the use of a much thinner, more flexible and so less stiff spiral wound element is envisaged. In fact, the use of a foil sheet-like spiral wound element has been found sufficient to adequately coil used blisters. The coils of this element are closely wound, preferably such that adjacent coils lie in contact with each other and there is no space between them in the absence of a used portion of a blister strip. As the spiral wound element is considerably more flexible than the spiral wound elements of previous embodiments, the frictional forces between the used portion of the blister strip and the spiral wound element are considerably reduced.

The coil of a used portion of the blister strip is formed in a different way with a more flexible spiral wound element as the spiral wound element begins to move as soon as it is contacted by the leading edge of the used portion of the blister strip. The steps in the formation of a coil of blisters are shown in the sequence of drawings of FIG. 19(a) to 19(j).

Figure 1A:
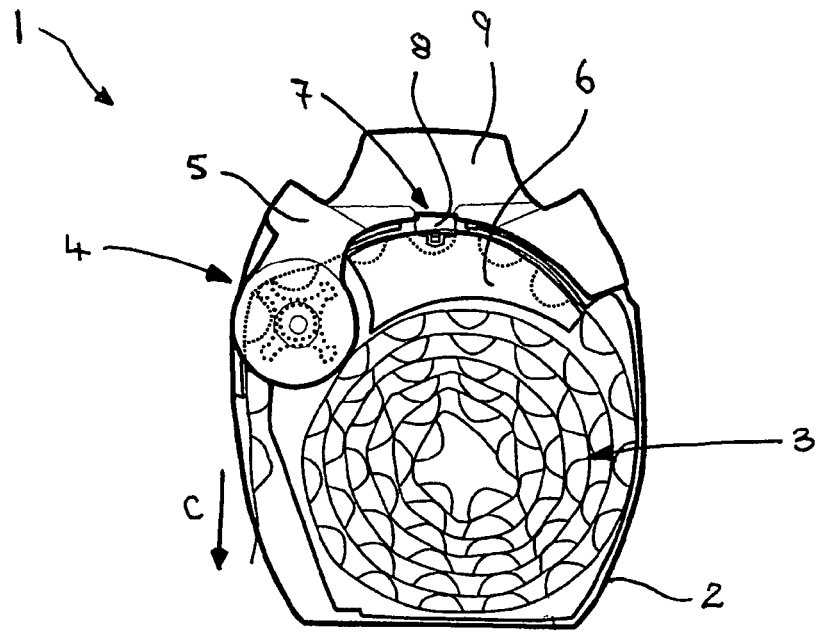
Figure 1B:
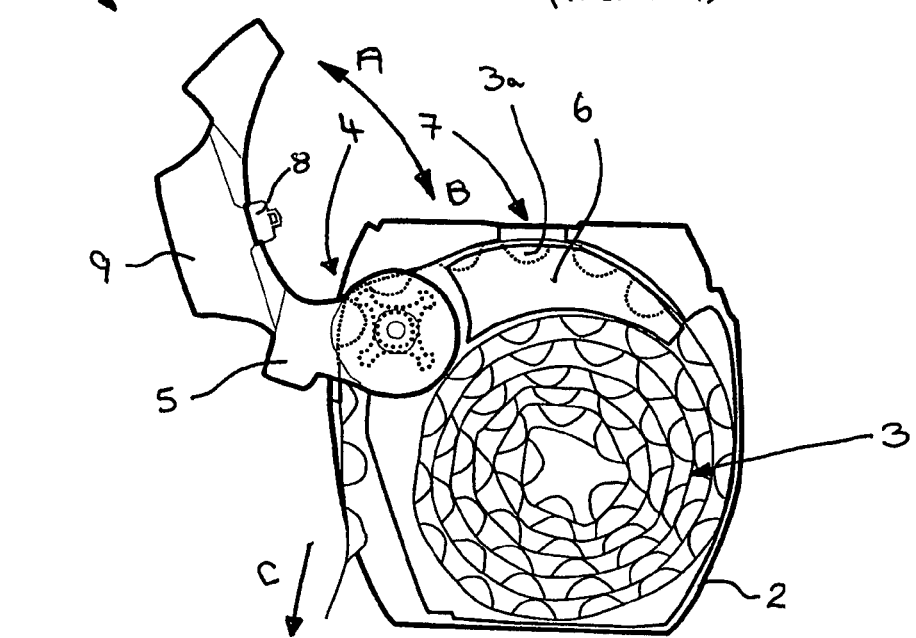
Figure 2:
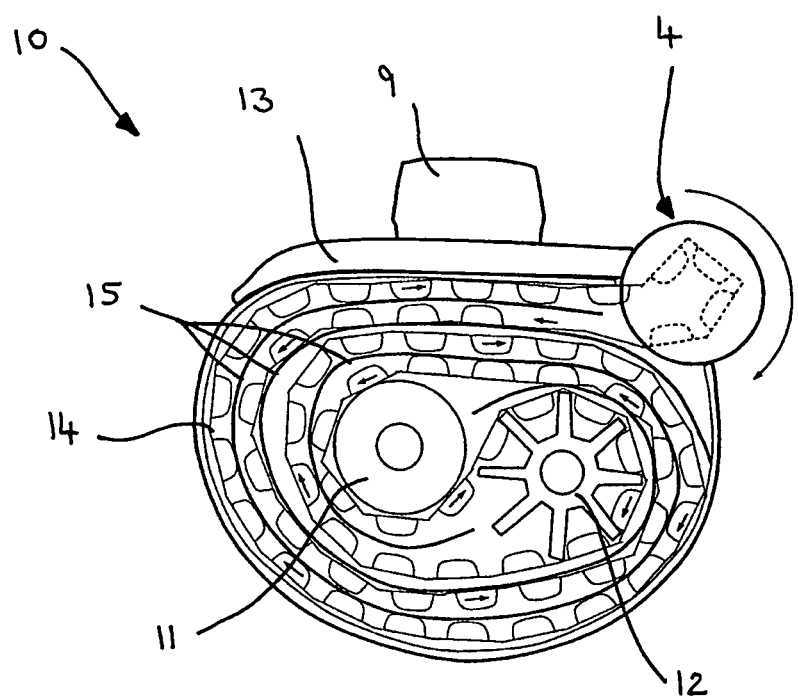
FIG. 2 is a sectional view of an inhalation device in which all the blisters are retained within the device and in which the blister strip takes the form of an endless loop which is wrapped around itself.
Figure 3A:
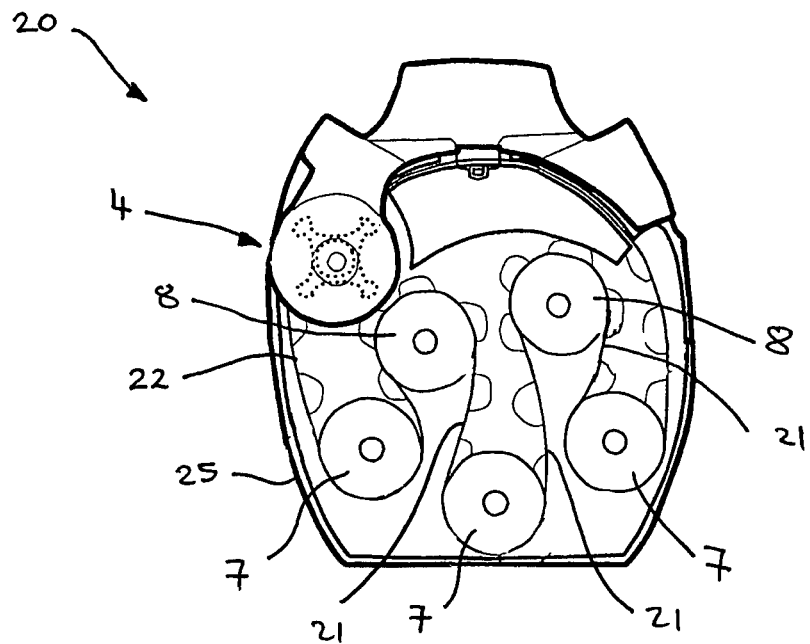
FIGS. 3a and 3b show front and rear sectional views of another version of a previously undisclosed endless loop device in which the strip is driven at several locations along its length.
Figure 3B:
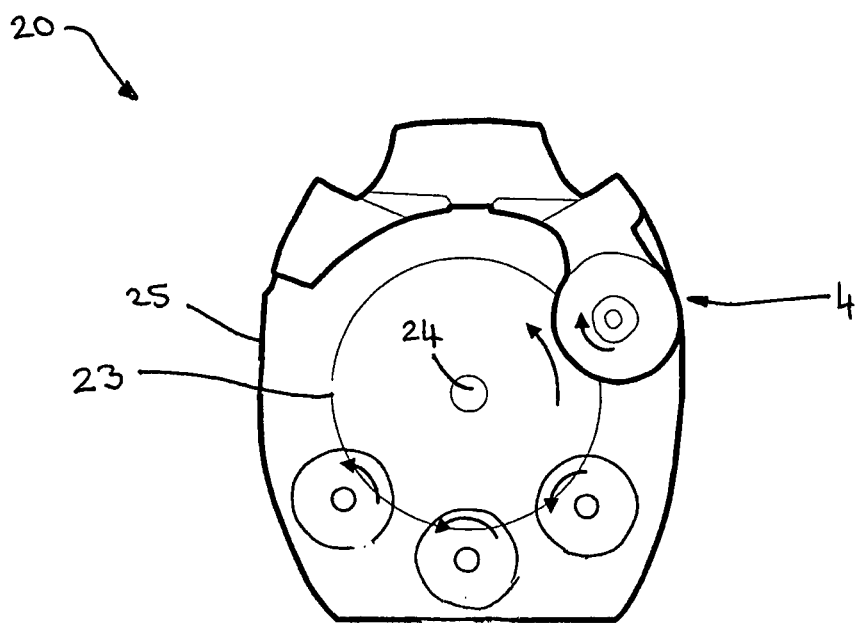

FIG. 19(a) shows a spiral wound element 150 in a stable unstressed state according to this embodiment of the invention which is formed from a flat elongate sheet of thin, flexible foil-like material. The walls of the spiral wound element 150 may all lie in contact although there may also be a space between the walls, as shown in FIG. 1(a).

FIG. 19(b) shows the same spiral wound element 150 as the leading edge 151a of a used portion of a blister strip 151 is received within the mouth 152 of the spiral wound element 150. At this point, the leading edge 151a has come into contact with the curved surface of the spiral wound element 150 but there is generally no flexing or deformation of the used portion of the blister strip 151 or the spiral wound element 150.

FIG. 19(c) shows the spiral wound element 150 after the used portion of the blister strip 151 has moved further towards the spiral wound element 150 and from which it can be seen that the strip 151 begins to flex as the leading edge 151a starts to travel up the curved inner wall surface of the outer coil of the spiral wound element 150, in the direction shown by arrow "A" in the Figure, and the outer coil of the spiral wound element 150 begins to move away from its adjacent inner coil and begin to straighten out due to the force of the leading end 151a of the relatively stiff used portion of the blister strip 151 against the flexible spiral wound element 150.

FIG. 19(d) shows the spiral wound element 150 after the used portion of the blister strip 151 has been moved further into or towards the spiral wound element 150 and from which it can be seen that the leading edge 151a of the blister strip 151 has travelled further up the curved inner surface of the outer coil and the blister strip 151 has deformed further pushing out and further straightening the outer coil and effectively unwinding or unrolling the spiral wound element 150, as can be seen from the position of the trailing end 153 of the spiral wound element 150.

FIG. 19(e) shows the spiral wound element 150 after the used portion of the blister strip 151 has been moved further towards the spiral wound element 150 and from which it can be seen that the leading edge 151a of the blister strip 151 has travelled yet further up the curved inner surface of the outer coil, the blister strip 151 further deforming and assuming a curved shape close to its leading edge 151a. Further unwinding or unrolling of the spiral wound element 150 is apparent due to the load applied to the spiral wound element 150 by the leading end 151a of the stiffer blister strip 151.

FIG. 19(f) shows the spiral wound element 150 after the used portion of the blister strip 151 has been moved even further forward toward and into the spiral wound element 150 and from which it can be seen that the leading edge 151a of the blister strip 151 is now almost parallel to the inner wall surface of the outer coil of the spiral wound element 150 with the lower surface 151b of the blister strip 151 generally in contact with the inner wall surface.

It will be appreciated that in the transition from the position shown in FIGS. 19(c) to 19(f), the direction of the force applied to the spiral wound element 150 by the leading end 151a of the used portion of the blister strip 151 changes. In FIG. 19(c), the direction in which the primary component "X" of the load acts against the spiral wound element 150 is at an angle "α" to a tangent extending along the wall surface of the spiral wound element 150 from the point of contact of the leading edge 151a of the strip 151 with the spiral wound element 150, which tends to cause the spiral wound element 150 to unroll or unwind. However, in FIG. 19(f) the primary component of the load acts at a much smaller angle to a tangent extending along the wall surface of the spiral wound element 150 from the point of contact of the leading edge 151a of the strip 151 with the spiral wound element 150 so that the strip 151 tends to more closely follow the wall surface of the spiral wound element 150 and slide along the wall surface so as to coil up within the spiral wound element 150 rather than continue to unroll or unwind it.

FIG. 19(g) to 19(i) shows the spiral wound element 150 after the used portion of the blister strip 151 has advanced further forward into the spiral wound element 150 and from which it can be seen that the strip 151 generally assumes a curvature which is similar to the curvature of the spiral wound element 150 and that the spiral wound element 150 begins to expand as more of the strip 151 is fed into it.

In FIG. 19(j), a complete closed coil of a used portion of the blister strip has been formed. As further blisters are used up, the spiral wound element 150 expands to accommodate more blisters and to form further coils.

The sequence of FIG. 19(a) to 19(j) demonstrates how deformation occurs with the spiral wound element 150 in isolation, i.e. without being acted on by any external forces resulting from, for example, contact of the spiral wound element against the walls of the housing of the device and/or against a flexible dividing wall separating the chamber into two regions containing used and unused portions of the blister strip, respectively.

FIGS. 20(a) to 20(f) show how deformation occurs in practice and when the spiral wound element 150 is constrained between the housing wall 160 below the spiral wound element 150 and a flexible dividing wall 90 above the spiral wound element 150 or, if no dividing wall 90 is present, the unused portion of the blister strip. Generally, the spiral wound element 150 deforms in the same way although, as can be seen from FIGS. 20(a) to 20(c), the spiral wound element 150 unrolls or unwinds along the end wall surface 160 of the housing 170 prior to expansion. The resulting coil formed from the used portion of the blister strip is also noticeably and usefully smaller than the coil created by an unconstrained spiral wound element.

In practice, it has been found that, when the spiral wound element 150 has expanded to the extent shown in FIGS. 20(d) and 20(e), the coil formed from the used portion of the blister strip becomes very loose due to the flexibility of the spiral wound element 150 which places a load on the coil which is insufficient to keep it close wound or tight. This problem can be mitigated by using the flexible dividing wall 90, the unused portion of the blister strip if no dividing wall is present, or some other dedicated element, to steady the spiral wound element 150 and used portion of the blister strip 151 as it expands, thereby preventing over expansion and maintaining relative tightness between the windings. As shown in FIGS. 20(a) to 20(f), expansion of the spiral wound element 150 is controlled, supported or at least steadied by its contact with the flexible dividing wall 90. As mentioned previously, the spiral wound element and flexible dividing wall may be at least partially attached to each other so that the dividing wall expands together with the spiral wound element, thereby providing additional control of expansion of the spiral wound element.

FIGS. 21(a) to 21(c) show the spiral wound element according to this embodiment of the invention. FIGS. 21(a) and 21(c) show the spiral wound element in its normal relaxed coiled state from which it can be seen that it has a generally planar or uncoiled leading edge portion 160 with slots 161 to facilitate its connection to corresponding lugs in the device housing. FIG. 21(b) shows a plan view of the spiral wound element after it has been flattened out. Table 1 shows preferred dimensions of the spiral wound element according to one preferred embodiment of the invention. As the diameter of a coiled strip of a used portion of a blister strip may exceed 50 mm, the diameter of the spiral wound element prior to receiving the strip may be less than 25% of its maximum diameter, i.e. when filled with a used portion of a strip of blisters having a diameter in the region of 50 mm.

TABLE 1

| | |
|---|---|
| Length (a) | ~104 mm |
| Width (b) | ~17.5 mm |
| Diameter (c) unstressed | ~12.4 mm |
| Length (d) of initial portion | ~16 mm |
| Thickness (e) of material | ~0.0508 mm |

Although embodiments of the invention have been described in which a spiral wound element is provided only for coiling up a used portion of a blister strip, it is also envisaged that a second spiral wound element could be provided to contain the unused blister strip. In this situation, the unused blister strip may be wound into a coil within a spiral wound element that is then located in the housing of the device during assembly. As the device is used, the spiral wound element containing the coiled up strip of unused blisters gradually retracts as the coil unwinds whereas the spiral wound element that receives the used portion of the strip expands as the used portion of the strip is coiled up within it. The spiral wound elements 130a,130b may be formed integrally as a single unit and be fixed to the housing 71 together, as shown in FIG. 17a which illustrates a "twin coil" spiral wound element 130 together with a strip 61a of unused blisters received therein and, FIG. 17b which illustrates the coil once loaded into an inhalation device 70 so as to form an integral part of the device. Since identical materials can be used for each spiral wound element 130a,130b, this reduces the overall component count and simplifies the assembly process. It will be appreciated that an aperture (not shown) may need to be made in the twin spiral wound element 130 at the blister piercing station 7 to allow the piercing elements 8 to extend through the aperture into a blister located beneath it.

In an alternative arrangement, it is envisaged that two separate spiral wound elements may be used. Means to fix the twin coil element to the device housing may take the same form as the slots 161 illustrated in FIG. 21. These slots may be formed, for example, in the spiral wound element between the two coils.

If a spiral wound element is used for the unused blister strip, the assembly of the device is greatly simplified because the coil of unused blisters is essentially preformed and held together in its coiled formation by the spiral wound element ready for insertion into the device during assembly. Preferably, the spiral wound element containing the unused blister strip is loaded into the housing of an inhaler together with the strip. However, it is envisaged that the coiled strip could be pressed out of the spiral wound element containing it immediately prior to or during insertion into the housing so that the unused strip is maintained in in its coiled state only by being constrained by the housing walls.

Blister strips are typically produced by a form/fill/seal machine which produces flat strips that must be wound into a coil prior to insertion into the device housing. Conventionally, this is achieved by gripping the end of a strip on a winding spindle and rotating the spindle until the coil is formed. Although this procedure works satisfactorily, the step of gripping the end of the strip is intricate and complex to automate. Therefore, it is advantageous to avoid having to locate and grip the strip. This is achieved with the spiral wound element of the present invention because the end of the strip can simply be fed into the mouth of the spiral wound element. As more of the strip is fed into the coil, it is wound up within it in the same way that the used blister strip is wound up within the inhalation device during use.

A sequence of drawings to show how a flat strip of unused blisters 120 which have been produced using a form/fill/seal blister strip forming machine (not shown) can be fed into and wound up within a spiral wound element 123 ready for insertion into the chamber of a device, is shown in FIGS. 18a to 18c. It will be appreciated that the strip can either be pre-cut or be cut as part of the winding process. The drive to the strip can be achieved with a driving wheel 121 and a pinch wheel 122 to give positive grip to the strip to drive it in the direction of the arrow "D" in the drawings.

As mentioned above, when the strip is fully wound it can be transferred into the device by sliding it axially out of the spiral wound element and into the device housing. Alternatively, the spiral wound element 123 ("former") can be loaded into the device housing together with the strip 120 to become a component of the device. The loaded spiral formers 123 can also be used to contain and protect the strip 120 during assembly or storage operations, as in this form it is more compact and more robust than a flat length of strip.

A variety of medicaments may be administered alone by using inhalers of the invention. Such medicaments include those that are suitable for the treatment of asthma, chronic obstructive pulmonary diseases (COPD), respiratory infections, rhinitis, allergic rhinitis, nasal diseases and disorders; general and specific conditions, and systemic diseases with the lung or nasal cavity as the site of delivery. Such medicaments include, but are not limited to, $\beta_2$-agonists, eg carmoterol, fenoterol, formoterol, levalbuterol, pirbuterol, reproterol, metaproterenol, rimiterol, salbutamol, salmeterol, indacaterol, terbutaline, orciprenaline, clenbuterol, bambuterol, procaterol, broxaterol, picumeterol, and bitolterol; non-selective $\beta$-stimulants such as ephedrine and isoprenaline; phosphodiesterase (PDE) inhibitors, eg methylxanthines, theophylline, aminophylline, choline theophyllinate, and selective PDE isoenzyme inhibitors, PDE 3 inhibitors, eg milrinone and motapizone; PDE 4 inhibitors, eg rolipram, cilomilast, roflumilast, oglemilast, and ONO 6126; PDE 3/4 inhibitors, eg zardaverine and tolafentrine; inducers of HDAC2 eg theophylline; anticholinergics including muscarinic receptor (M1, M2, and M3) antagonists eg atropine, hyoscne, glycopyrrolate, ipratroplum, tiotropium, oxitropium, NVA237, pirenzepine, and telenzepine; mast cell stabilisers, eg cromoglycate and ketotifen; bronchial anti-inflammatory agents, eg nedocromil; steroids, eg beclometasone, dexamethasone, fluticasone, budesonide, flunisolide, rofleponide, triamcinolone, butixocort, mometasone, and ciclesonide; disease modifying agents such as methotrexate, leflunomide, teriflunomide, and hydroxychloroquine; histamine type 1 receptor antagonists, eg cetirizine, loratadine, desloratadine, fexofenadine, acrivastine, terfenadine, astemizole, azelastine, levocabastine, chlorpheniramine, promethazine, cyclizine, and mizolastine; antibacterial agents and agents for cystic fibrosis and/or tuberculosis treatment, eg Pseudomonas aeruginosa infection vaccines (eg Aerugen®), mannitol, denufosol, glutathione, N-acetylcysteine, amikacin duramycin, gentamycin, tobramycin, dornase alfa, alpha 1-antitrypsin, heparin, dextran, capreomycin, vancomycin, meropenem, ciprofloxacin, piperacillin, and rifampicin; mucolytic agents for the treatment of COPD and cystic fibrosis, eg N-acetylcysteine, and ambroxol; histamine type 2 receptor antagonists; tachykinin neurokinin antagonists; triptans, eg almotriptan, rizatriptan, naratriptan, zolmitriptan, sumatritpan, eletriptan, and frovatriptan; neurological agents eg apomorphine, dronabinol, dihydroergotamine, and loxapine; antiviral agents eg foscarnet, acyclovir, famciclovir, valacyclovir, ganciclovir, cidofovir; amantadine, rimantadine; ribavirin; zanamivir and oseltamavir and pleconaril, protease inhibitors (eg ruprintrivir, indinavir, nelfinavir, ritonavir, and saquinavir), nucleoside reverse transcriptase inhibitors (eg didanosine, lamivudine, stavudine, zalcitabine, and zidovudine), and non-nucleoside reverse transcriptase inhibitors (eg nevirapine and efavirenz); $\alpha$-1/$\alpha$-2 adrenoceptor agonists, eg propylhexedrine, phenylephrine, phenylpropanolamine, ephedrine, pseudoephedrine, naphazoline, oxymetazoline, tetrahydrozoline, xylometazoline, tramazoline, and ethylnorepinephrine; platelet aggregation inhibitors/anti-inflammatory agents, eg bemiparin, enoxaparin, heparin; anti-infectives, eg cephalosporins, penicillins, tetracyclines, macrolides, beta-lactams, flouroquinolones, streptomycin, sulphonamides, aminoglycosides (eg tobramycin), doripenem, pentamidine, colistimethate, and aztreonam; agents for sexual health, sexual dysfunction including premature ejaculation; eg. apomorphine, VR776, agents that acts via 5HT- and noradrenergic-mediated pathways in the brain, leuprolide, and PDE 5 inhibitors eg, sildenafil, tadalafil, and vardenafil; leukotriene modifiers, eg zileuton, fenleuton, tepoxalin, montelukast, zafirlukast, ontazolast, ablukast, pranlikast, verlukast, and iralukast; inducible nitric oxide synthase (iNOS) inhibitors; antifungals, eg amphotericin B, natamycin, and nystatin; analgesics, eg codeine, dihydromorphine, ergotamine, fentanyl, cannabinoids, and morphine; anxiolytic/antidepressive agents, eg benzodiazepines and benzodiazepine derivatives, diazepam, midazolam, chlordiazepoxide, lorazepam, oxazepam, clobazam, alprazolam, clonazepam, flurazepam, zolazepam; tryptase and elastase inhibitors; beta-2 integrin antagonists; adenosine receptor agonists or antagonists, eg adenosine 2$\alpha$ agonists; calcium channel blockers, eg gallopamil, and diltiazem; prostacyclin analogues, eg iloprost; endothelin-receptor antagonists, eg LU-135252; cytokine antagonists, eg chemokine antagonists and inhibitors and modifiers of cytokine synthesis including modifiers and inhibitors of the pro-inflammatory transcription factor, NFkB; interleukins and inhibitors of interleukins, eg aldesleukin; therapeutic proteins and peptides, eg insulin, insulin aspart, insulin glulisine; insulin lispro, neutral, regular and soluble insulins, isophane insulins, insulin zinc, protamine zinc insulin, insulin analogues, acylated insulin, insulin glargine, insulin detemir, glucagon, glucagon-like peptides, and exendins; enzymes, eg dornase alfa; systemically active macromolecules, eg human growth hormone, leuprolide, alpha-interferon, growth factors (eg insulin-like growth factor type 1), hormones, eg epinephrine, testosterone, and parathyroid hormone and analogues (eg Ostabolin-C); osteoporosis agents, eg bisphosphonates; anticancer agents, eg anthracyclines, doxorubicin, idarubicin, epirubicin, methotrexate, taxanes, paclitaxel, docetaxel, ciplatin, vinca alkaloids, vincristine, and 5-fluorouracil; anticoagulants, eg blood factors and blood factor constructs, eg FVIII-Fc and FIX-Fc;, eg FV111-Fc; immunomodulators, eg cyclosporine, sirolimus, and tacrolimus; antiproliferative immunosuppressants, eg azathioprine, and mycophenolate mofetil; cytokines (eg interferons, interferon $\beta$, interleukins, and interleukin antagonists and inhibitors); nucleic acids; vaccines, eg flumist; anti-obesity agents; diagnostics and gene therapies. It will be clear to a person skilled in the art that, where appropriate, the medicaments may be linked to a carrier molecule or molecules and/or used in the form of prodrugs, salts, as esters, or as solvates to optimize the activity and/or stability of the medicament.

Inhalers according to the invention may also be used to deliver combinations of two or more different medicaments. Specific combinations of two medicaments which may be mentioned include combinations of steroids and $\beta_2$-agonists.

Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol. Specifically inhalers according to the invention may also be used to deliver combinations of three different medicaments.

It will be clear to a person skilled in the art that, where appropriate, the medicaments may be linked to a carrier molecule or molecules and/or used in the form of prodrugs, salts, as esters, or as solvates to optimize the activity and/or stability of the medicament.

It is also envisaged that the pharmaceutical composition may comprise one or more, preferably one, anticholinergic 1, optionally in combination with a pharmaceutically acceptable excipient.

The anticholinergic 1 can be selected from the group consisting of
a) tiotropium salts 1a,
b) compounds of formula 1c

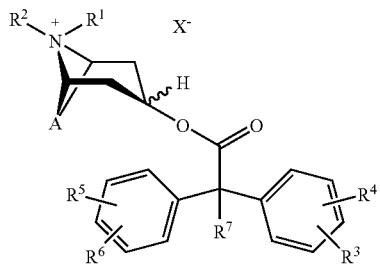

wherein
A denotes a double-bonded group selected from among

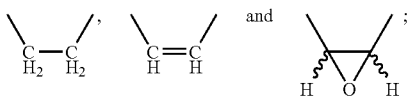

$X^-$ denotes an anion with a single negative charge, preferably an anion selected from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate, $R^1$ and $R^2$ which may be identical or different denote a group selected from among methyl, ethyl, n-propyl and iso-propyl, which may optionally be substituted by hydroxy or fluorine, preferably unsubstituted methyl;

$R^3$, $R^4$, $R^5$ and $R^6$, which may be identical or different, denote hydrogen, methyl, ethyl, methyloxy, ethyloxy, hydroxy, fluorine, chlorine, bromine, CN, $CF_3$ or $NO_2$;

$R^7$ denotes hydrogen, methyl, ethyl, methyloxy, ethyloxy, —$CH_2$—F, —$CH_2$—$CH_2$—F, -0-$CH_2$—F, -0-$CH_2$—$CH_2$—F, —$CH_2$—OH, —$CH_2$—$CH_2$—OH, $CF_3$, —$CH_2$—OMe, —$CH_2$—$CH_2$—OMe, —$CH_2$—OEt, —$CH_2$—$CH_2$—OEt, —O—COMe, —O—COEt, -Q-COCF$_3$, -Q-COCF$_3$, fluorine, chlorine or bromine;

c) compounds of formula 1d

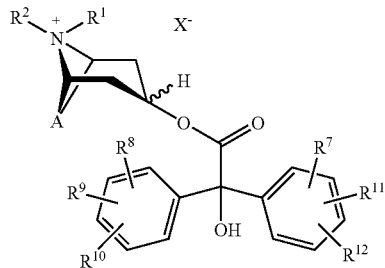

wherein
A, $X^-$, $R^1$ and $R^2$ may have the meanings as mentioned hereinbefore and wherein $R^7$, $R^8$, $R^9$, $R^{10}$, $R^{11}$ and $R^{12}$, which may be identical or different, denote hydrogen, methyl, ethyl, methyloxy, ethyloxy, hydroxy, fluorine, chlorine, bromine, CN, $CF_3$ or $NO_2$, with the proviso that at least one of the groups $R^7$, $R^8$, $R^9$, $R^{10}$, $R^{11}$ and $R^{12}$ is not hydrogen, d) compounds of formula 1e

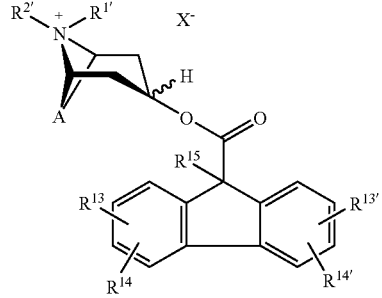

wherein A and $X^-$ may have the meanings as mentioned hereinbefore, and wherein
$R^{15}$ denotes hydrogen, hydroxy, methyl, ethyl, —$CF_3$, $CHF_2$ or fluorine;
$R^{1'}$ and $R^{2'}$ which may be identical or different denote $C_1$-$C_5$-alkyl which may optionally be substituted by $C_3$-$C_6$-cycloalkyl, hydroxy or halogen, or $R^{1'}$ and $R^{2'}$ together denote a —$C_3$-$C_5$-alkylene-bridge;
$R^{13}$, $R^{14}$, $R^{13'}$ and $R^{14'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen, e) compounds of formula 1f

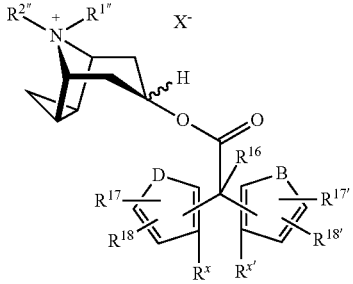

wherein $X^-$ may have the meanings as mentioned hereinbefore, and wherein
D and B which may be identical or different, preferably identical, denote —O—, —S—, —NH—, —$CH_2$—, —CH=CH, or —N($C_1$-$C_4$-alkyl)-;
$R^{16}$ denotes hydrogen, hydroxy, —$C_1$-$C_4$-alkyl, —$C_1$-$C_4$-alkyloxy, —$C_1$-$C_4$-alkylene-Halogen, —O—$C_1$-

$C_4$alkylene-halogen, —$C_1$-$C_4$-alkylene-OH, —$CF_3$, $CHF_2$, —$C_1$-$C_4$-alkylene-$C_1$-$C_4$alkyloxy, —O—$COC_1$-$C_4$-alkyl, —O—$COC_1$—$C_4$-alkylene-halogen, —$C_1$-$C_4$-alkylene-$C_3$-$C_6$-cycloalkyl, —O—$COCF_3$ or halogen;

$R^{1'''}$ and $R^{2'''}$ which may be identical or different, denote —$C_1$-$C_5$-alkyl, which may optionally be substituted by —$C_3$-$C_6$-cycloalkyl, hydroxy or halogen, or $R^{1'''}$ and $R^{2'''}$ together denote a —$C_3$-$C_5$-alkylene bridge;

$R^{17}$, $R^{18}$, $R^{17'}$ and $R^{18'}$, which may be identical or different, denote hydrogen, $C_1$-$C_4$-alkyl, $C_1$-$C_4$-alkyloxy, hydroxy, —$CF_3$, —$CHF_2$, CN, $NO_2$ or halogen;

$R^x$ and $R^{x'}$ which may be identical or different, denote hydrogen, $C_1$-$C_4$-alkyl, $C_1$-$C_4$-alkyloxy, hydroxy, —$CF_3$, —$CHF_2$, CN, $NO_2$ or halogen or $R^x$ and $R^{x'}$ together denote a single bond or a bridging group selected from among the bridges —O—, —S—, —NH—, —$CH_2$—, —$CH_2$—$CH_2$—, —N($C_1C_4$-alkyl), —CH($C_1$-$C_4$-alkyl)- and —C($C_1$-$C_4$-alkyl)$_2$, and f) compounds of formula 1g

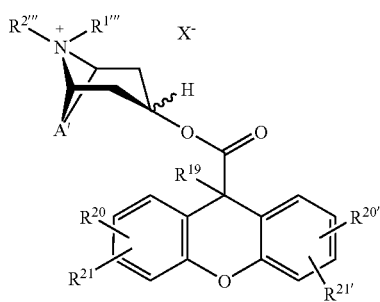

wherein $X^-$ may have the meanings as mentioned hereinbefore, and wherein

A' denotes a double-bonded group selected from among

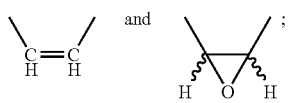

$R^{19}$ denotes hydroxy, methyl, hydroxymethyl, ethyl, —$CF_3$, $CHF_2$ or fluorine;

$R^{1'''}$ and $R^{2'''}$ which may be identical or different denote $C_1$-$C_5$-alkyl which may optionally be substituted by $C_3$-$C_6$-cycloalkyl, hydroxy or halogen, or $R^{1'''}$ and $R^{2'''}$ together denote a —$C_3$-$C_5$-alkylene-bridge;

$R^{20}$, $R^{21}$, $R^{20'}$ and $R^{21'}$ which may be identical or different denote hydrogen, —

$C_1$-$C_4$-alkyl, —$C_1$-$C_4$-alkyloxy, hydroxy, —$CF_3$, —$CHF_2$, CN, $NO_2$ or halogen.

The compounds of formula 1c are known in the art (WO 02/32899).

In a preferred embodiment of the invention the method comprises administration of compounds of formula 1c, wherein $X^-$ denotes bromide;

$R^1$ and $R^2$ which may be identical or different denote a group selected from methyl and ethyl, preferably methyl;

$R^3$, $R^4$, $R^5$ and $R^6$, which may be identical or different, denote hydrogen, methyl, methyloxy, chlorine or fluorine;

$R^7$ denotes hydrogen, methyl or fluorine, optionally together with a pharmaceutically acceptable excipient.

Of particular importance are compounds of general formula 1c, wherein A denotes a double-bonded group selected from among

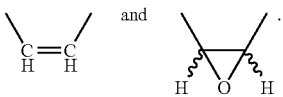

The compounds of formula 1c, may optionally be administered in the form of the individual optical isomers, mixtures of the individual enantiomers or racemates thereof.

Of particular importance within a method according to the invention are the following compounds of formula 1c:

tropenol 2,2-diphenylpropionic acid ester methobromide, scopine 2,2-diphenylpropionic acid ester methobromide, scopine 2-fluoro-2,2-diphenylacetic acid ester methobromide and tropenol 2-fluoro-2,2-diphenylacetic acid ester methobromide.

The compounds of formula 1d are known in the art (WO 02/32898).

In a preferred embodiment of the invention the method comprises administration of compounds of formula 1d, wherein A denotes a double-bonded group selected from among

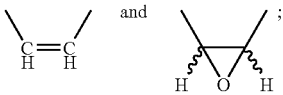

$X^-$ denotes bromide;

$R^1$ and $R^2$ which may be identical or different denote methyl or ethyl, preferably methyl;

$R^7$, $R^8$, $R^9$, $R^{10}$, $R^{11}$ and $R^{12}$, which may be identical or different, denote hydrogen, fluorine, chlorine or bromine, preferably fluorine with the proviso that at least one of the groups $R^7$, $R^8$, $R^9$, $R^{10}$, $R^{11}$ and $R^{12}$ not hydrogen, optionally together with a pharmaceutically acceptable excipient.

Of particular importance within the method according to the invention are the following compounds of formula 1d:

tropenol 3,3',4,4'-tetrafluorobenzilic acid ester methobromide, scopine 3,3',4,4'-tetrafluorobenzilic acid ester methobromide, scopine 4,4'-difluorobenzilic acid ester methobromide, tropenol 4,4'-difluorobenzilic acid ester methobromide, scopine 3,3'-difluorobenzilic acid ester methobromide, and tropenol 3,3'-difluorobenzilic acid ester methobromide.

The pharmaceutical compositions according to the invention may contain the compounds of formula 1d optionally in the form of the individual optical isomers, mixtures of the individual enantiomers or racemates thereof.

The compounds of formula 1e are known in the art (WO 03/064419).

In a preferred embodiment of the invention the method comprises administration of compounds of formula 1e, wherein A denotes a double-bonded group selected from among

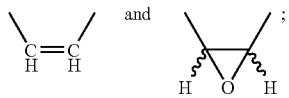

X⁻ denotes an anion selected from among chloride, bromide and methanesulphonate, preferably bromide;
$R^{15}$ denotes hydroxy, methyl or fluorine, preferably methyl or hydroxy;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen, —CF$_3$, —CHF$_2$ or fluorine, preferably hydrogen or fluorine, optionally together with a pharmaceutically acceptable excipient.

In another preferred embodiment of the invention the method comprises administration of compounds of formula 1e, wherein
A denotes a double-bonded group selected from among

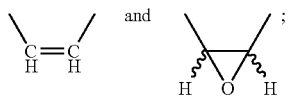

X⁻ denotes bromide;
$R^{15}$ denotes hydroxy or methyl, preferably methyl;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen or fluorine, optionally together with a pharmaceutically acceptable excipient.

Of particular importance within the method according to the invention are the following compounds of formula 1e:
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide.

The pharmaceutical compositions according to the invention may contain the compounds of formula 1e optionally in the form of the individual optical isomers, mixtures of the individual enantiomers or racemates thereof.

The compounds of formula 1f are known in the art (WO 03/064418).

In another preferred embodiment of the invention the method comprises administration of compounds of formula 1f wherein
X⁻ denotes chloride, bromide, or methanesulphonate, preferably bromide;
D and B which may be identical or different, preferably identical, denote —O, —S, —NH or —CH=CH—;
$R^{16}$ denotes hydrogen, hydroxy, —C$_1$-C$_4$-alkyl, —C$_1$-C$_4$ alkyloxy, —CF$_3$, —CHF$_2$, fluorine, chlorine or bromine;
$R^{1'''}$ and $R^{2'''}$ which may be identical or different, denote C$_1$-C$_4$-alky, which may optionally be substituted by hydroxy, fluorine, chlorine or bromine, or $R^{1'''}$ and $R^{2'''}$ together denote a —C$_3$-C$_4$-alkylene-bridge;
$R^{17}$, $R^{18}$, $R^{17'}$ and $R^{18'}$, which may be identical or different, denote hydrogen, C$_1$-C$_4$-alkyl, C$_1$-C$_4$-alkyloxy, hydroxy, —CF$_3$, —CHF$_2$, CN, NO$_2$, fluorine, chlorine or bromine;

$R^x$ and $R^{x'}$ which may be identical or different, denote hydrogen, C$_1$-C$_4$-alkyl, C$_1$-C$_4$-alkyloxy, hydroxy, —CF$_3$, —CHF$_2$, CN, NO$_2$, fluorine, chlorine or bromine or
$R^x$ and $R^{x'}$ together denote a single bond or a bridging group selected from among the bridges —O—, —S—, —NH— and —CH$_2$—, optionally together with a pharmaceutically acceptable excipient.

In another preferred embodiment of the invention the method comprises administration of compounds of formula 1f, wherein
X⁻ denotes chloride, bromide, or methanesulphonate, preferably bromide;
D and B which may be identical or different, preferably identical, denote —S or —CH=CH—;
$R^{16}$ denotes hydrogen, hydroxy or methyl;
$R^{1'''}$ and $R^{2'''}$ which may be identical or different, denote methyl or ethyl;
$R^{17}$, $R^{18}$, $R^{17'}$ and $R^{18'}$, which may be identical or different, denote hydrogen, —CF$_3$ or fluorine, preferably hydrogen;
$R^x$ and $R^{x'}$ which may be identical or different, denote hydrogen, —CF$_3$ or fluorine, preferably hydrogen or
$R^x$ and $R^{x'}$ together denote a single bond or the bridging group —O—, optionally together with a pharmaceutically acceptable excipient.

In another preferred embodiment of the invention the method comprises administration of compounds of formula 1f wherein
X⁻ denotes bromide;
D and B denote —CH=CH—;
$R^{16}$ denotes hydrogen, hydroxy or methyl;
$R^{1'''}$ and $R^{2'''}$ denote methyl;
$R^{17}$, $R^{18}$, $R^{17'}$ and $R^{18'}$, which may be identical or different, denote hydrogen or fluorine, preferably hydrogen;
$R^x$ and $R^{x'}$ which may be identical or different, denote hydrogen or fluorine, preferably hydrogen or
$R^x$ and $R^{x'}$ together denote a single bond or the bridging group —O—, optionally together with a pharmaceutically acceptable excipient.

Of particular importance within the method according to the invention are the following compounds of formula 1f:
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.

The pharmaceutical compositions according to the invention may contain the compounds of formula 1f optionally in the form of the individual optical isomers, mixtures of the individual enantiomers or racemates thereof.

The compounds of formula 1g are known in the art (WO 03/064417).

In another preferred embodiment of the invention the method comprises administration of compounds of formula 1g wherein A' denotes a double-bonded group selected from among

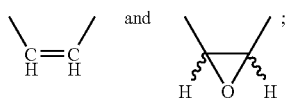

X⁻ denotes chloride, bromide or methanesulphonate, preferably bromide;
$R^{19}$ denotes hydroxy or methyl;
$R^{1'''}$ and $R^{2'''}$ which may be identical or different represent methyl or ethyl, preferably methyl;
$R^{20}$, $R^{21}$, $R^{20'}$ and $R^{21'}$ which may be identical or different represent hydrogen, —$CF_3$, —$CHF_2$ or fluorine, preferably hydrogen or fluorine, optionally together with a pharmaceutically acceptable excipient.

In another preferred embodiment of the invention the method comprises administration of compounds of formula 1g wherein
A' denotes a double-bonded group selected from among

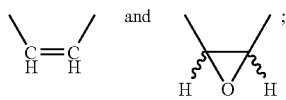

X⁻ denotes bromide;
$R^{19}$ denotes hydroxy or methyl, preferably methyl;
$R^{1'''}$ and $R^{2'''}$ which may be identical or different represent methyl or ethyl, preferably methyl;
$R^3$, $R^4$, $R^{3'}$ and $R^{4'}$ which may be identical or different represent hydrogen or fluorine, optionally together with a pharmaceutically acceptable excipient.

Of particular importance within the method according to the invention are the following compounds of formula 1g:
  tropenol 9-hydroxy-xanthene-9-carboxylate methobromide;
  scopine 9-hydroxy-xanthene-9-carboxylate methobromide;
  tropenol 9-methyl-xanthene-9-carboxylate methobromide;
  scopine 9-methyl-xanthene-9-carboxylate methobromide;
  tropenol 9-ethyl-xanthene-9-carboxylate methobromide;
  tropenol 9-difluoromethyl-xanthene-9-carboxylate methobromide;
  scopine 9-hydroxymethyl-xanthene-9-carboxylate methobromide.

The pharmaceutical compositions according to the invention may contain the compounds of formula 1g optionally in the form of the individual optical isomers, mixtures of the individual enantiomers or racemates thereof.

The alkyl groups used, unless otherwise stated, are branched and unbranched alkyl groups having 1 to 5 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The cycloalkyl groups used, unless otherwise stated, are alicyclic groups with 3 to 6 carbon atoms. These are the cyclopropyl, cyclobutyl, cyclopentyl and cyclohexyl groups. According to the invention cyclopropyl is of particular importance within the scope of the present invention.

The alkylene groups used, unless otherwise stated, are branched and unbranched double- bonded alkyl bridges with 1 to 5 carbon atoms. Examples include: methylene, ethylene, propylene or butylene.

The alkylene-halogen groups used, unless otherwise stated, are branched and unbranched double-bonded alkyl bridges with 1 to 4 carbon atoms which may be mono-, di- or trisubstituted, preferably disubstituted, by a halogen. Accordingly, unless otherwise stated, the term alkylene-OH groups denotes branched and unbranched double-bonded alkyl bridges with 1 to 4 carbon atoms which may be mono-, di- or trisubstituted, preferably monosubstituted, by a hydroxy.

The alkyloxy groups used, unless otherwise stated, are branched and unbranched alkyl groups with 1 to 5 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

The alkylene-alkyloxy groups used, unless otherwise stated, are branched and unbranched double-bonded alkyl bridges with 1 to 5 carbon atoms which may be mono-, di- or trisubstituted, preferably monosubstituted, by an alkyloxy group.

The —O—CO-alkyl groups used, unless otherwise stated, are branched and unbranched alkyl groups with 1 to 4 carbon atoms which are bonded via an ester group. The alkyl groups are bonded directly to the carbonylcarbon of the ester group. The term —O—CO-alkyl-halogen group should be understood analogously. The group —O—CO—$CF_3$ denotes trifluoroacetate.

Within the scope of the present invention halogen denotes fluorine, chlorine, bromine or iodine. Unless otherwise stated, fluorine and bromine are the preferred halogens. The group CO denotes a carbonyl group.

One aspect of the invention is directed to an inhalation device, in which the plural of doses are contained in one reservoir. In another aspect of the invention, the inhalation device comprises the plural of doses in a multi-dose blister pack. In another aspect of the invention the inhalation device comprises the multi-dose blister pack in form of blister strip.

The inhalation device according to the invention comprises the compounds of formula 1 preferably in admixture with a pharmaceutically acceptable excipient to form a powder mixture. The following pharmaceutically acceptable excipients may be used to prepare these inhalable powder mixtures according to the invention: monosaccharides (e.g. glucose or arabinose), disaccharides (e.g. lactose, saccharose, maltose, trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose and trehalose are the particularly preferred excipients, while lactose, preferably in form of its monohydrate is most particularly preferred.

The compounds of formula 1 may be used in the form of their racemates, enantiomers or mixtures thereof. The separation of enantiomers from the racemates may be carried out using methods known in the art (e.g. by chromatography on chiral phases, etc.).

Optionally, the inhalation device according to the invention contains plural of doses of a medicament in powder form that contains, beside one compound of formula 1, another active ingredient.

Preferably the additional active ingredient is a beta$_2$ agonists 2 which is selected from the group consisting of albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-OXO-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

According to the instant invention more preferred beta2 agonists 2 are selected from the group consisting of bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-0X0-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino) ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

More preferably, the betamimetics 2 used as within the compositions according to the invention are selected from among fenoterol, formoterol, salmeterol, 3-(4-{6-[2-Hydroxy-2-(4-hydroxy-3-hydroxymethyl-phenyl)-ethylamino]-hexyloxy}-butyl)- benzenesulfoneamide, 5-[2-(5,6-Diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, the enantiomers, the diastereomers and optionally the pharmacologically acceptable acid addition salts thereof, and the hydrates thereof. Of the betamimetics mentioned above the compounds formoterol, salmeterol, 3-(4-{6-[2-Hydroxy-2-(4-hydroxy-3-hydroxymethyl-phenyl)-ethylamino]-hexyloxy}-butyl)-benzenesulfoneamide, and 5-[2-(5,6-Diethyl-indan-2-ylamino)-1-hydroxy-ethyl]-8-hydroxy-1H-quinolin-2-one are particularly preferred, optionally in the form of the racemates, the enantiomers, the diastereomers and optionally the pharmacologically acceptable acid addition salts thereof, and the hydrates thereof. Of the betamimetics mentioned above the compounds formoterol and salmeterol are particularly preferred, optionally in the form of the racemates, the enantiomers, the diastereomers and optionally the pharmacologically acceptable acid addition salts thereof, and the hydrates thereof.

Examples of pharmacologically acceptable acid addition salts of the betamimetics 2 according to the invention are the pharmaceutically acceptable salts which are selected from among the salts of hydrochloric acid, hydrobromic acid, sulphuric acid, phosphoric acid, methanesulphonic acid, acetic acid, fumaric acid, succinic acid, lactic acid, citric acid, tartaric acid, 1-hydroxy-2-naphthalenecarboxylic acid, 4-phenylcinnamic acid, 5-(2.4-difluorophenyl)salicylic acid or maleic acid. If desired, mixtures of the abovementioned acids may also be used to prepare the salts 2.

According to the invention, the salts of the betamimetics 2 selected from among the hydrochloride, hydrobromide, sulphate, phosphate, fumarate, methanesulphonate, 4-phenylcinnamate, 5-(2.4-difluorophenyl)salicylate, maleate and xinafoate are preferred. Particularly preferred are the salts of 2 in the case of salmeterol selected from among the hydrochloride, sulphate, 4-phenylcinnamate, 5-(2.4-difluorophenyl)salicylate and xinafoate, of which the 4-phenylcinnamate, 5-(2.4-difluorophenyl)salicylate and especially xinafoate are particularly important. Particularly preferred are the salts of 2 in the case of formoterol selected from the hydrochloride, sulphate and fumarate, of which the hydrochloride and fumarate are particularly preferred. Of exceptional importance according to the invention is formoterol fumarate.

Salts of salmeterol, formoterol, 3-(4-{6-[2-Hydroxy-2-(4-hydroxy-3-hydroxymethyl- phenyl)-ethylamino]-hexyloxy}-butyl)-benzenesulfoneamide, and 5-[2-(5,6-Diethyl-indan-2-ylamino)-1-hydroxy-ethyl]-8-hydroxy-1H- quinolin-2-one, are preferably used as the betamimetics 2 according to the invention. Of particular importance according to the invention are salmeterol and formoterol salts. Any reference to the term betamimetics 2 also includes a reference to the relevant enantiomers or mixtures thereof. In the pharmaceutical compositions according to the invention, the compounds 2 may be present in the form of their racemates, enantiomers or mixtures thereof. The separation of the enantiomers from the racemates may be carried out using methods known in the art (e.g. by chromatography on chiral phases, etc.) If the compounds 2 are used in the form of their enantiomers, it is particularly preferable to use the enantiomers in the R configuration at the C—OH group.

Optionally, the inhalation device according to the invention contains plural of doses of a medicament in powder form, that contains beside one compound of formula 1 a steroid 3 as another active ingredient.

In such medicament combinations the steroid 3 is preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11[beta]-hydroxy-16α-methyl-3-oxo-androsta-1,4-diene-17β-carbothionate, (S)-(2-oxo-tetrahydro-furan-3S-yl)6α,9α-difluoro-11β-hydroxy-16α-methyl-3-oxo-17α-propionyloxy-androsta-1,4-diene-17β-carbothionate, and etiprednol-dichloroacetate (BNP-166), optionally in the form of the racemates, enantiomers or diastereomers thereof and optionally in the form of the salts and derivatives thereof, the solvates and/or hydrates thereof.

In particularly preferred medicament combinations the steroid 3 is selected from the group comprising flunisolide, beclomethasone, triamcinolone, budesonide, fluticasone, mometasone, ciclesonide, rofleponide, ST-126, dexamethasone, (S)-fluoromethyl 6α,9α-difluoro-1Ia-[(2-furanylcarbonyl)oxy]-11β-hydroxy-16α-methyl-3-oxo-androsta-1,4-diene-17β-carbothionate, (S)-(2-oxo-tetrahydro-furan-3S-yl)6α,9α-difluoro-11β-hydroxy-16α-methyl-3-oxo-17α-propionyloxy-androsta-1,4-diene-17β-carbothionate, and etiprednol-dichloroacetate, optionally in the form of the racemates, enantiomers or diastereomers thereof and optionally in the form of the salts and derivatives thereof, the solvates and/or hydrates thereof.

In particularly preferred medicament combinations the steroid 3 is selected from the group comprising budesonide, fluticasone, mometasone, ciclesonide, (S)-fluoromethyl 6α,9α-difluoro-1Ia-[(2-furanylcarbonyl)oxy]-11β-hydroxy-16α-methyl-3-oxo-androsta-1,A-diene-17β-carbothionate, and etiprednol-dichloroacetate, optionally in the form of the racemates, enantiomers or diastereomers thereof and optionally in the form of the salts and derivatives thereof, the solvates and/or hydrates thereof.

Any reference to steroids 3 includes a reference to any salts or derivatives, hydrates or solvates thereof which may exist. Examples of possible salts and derivatives of the steroids 3 may be: alkali metal salts, such as for example sodium or potassium salts, sulphobenzoates, phosphates, isonicotinates, acetates, propionates, dihydrogen phosphates, palmitates, pivalates or furcates.

Optionally, the inhalation device according to the invention contains plural of doses of a medicament on powder form, that contains beside one compound of formula 1 additionally both, one of the betamimetics 2 mentioned hereinbefore and one of the steroids 3 mentioned hereinbefore.

Accordingly, in a preferred embodiment the invention relates to an inhalation device comprising a housing and a blister strip, the strip being movable to sequentially align each blister with means for opening a blister to enable a user to inhale said dose and, a spiral wound element to receive and coil the strip, wherein each blister contains a pharmaceutical composition in powder form wherein the pharmaceutical composition comprises one or more, preferably one, compound of formula 1.

In another embodiment, the invention relates to an inhalation device comprising a housing and a blister strip, the strip being movable to sequentially align each blister with means for opening a blister to enable a user to inhale said dose, the housing comprising a common chamber to receive the blister strip and a coil of breached blisters of that strip, the chamber being configured so that the coil of breached blisters occupies more of the space in the chamber initially occupied by the blister strip as more of the blisters of the strip are breached, wherein each blister contains a pharmaceutical composition in powder form wherein the pharmaceutical composition comprises one or more, preferably one, compound of formula 1.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronized active substance I—, and optionally 2 and/or 3, preferably with an average particle size of 0.5 to 10 μm, more preferably from 1 to 6 μm, is added to the excipient mixture. Processes for producing the inhalable powders according to the invention by grinding and micronizing and finally mixing the ingredients together are known from the prior art.

For the methods of preparing the pharmaceutical compositions in powder form reference may be made to the disclosure of WO 02/30390, WO 03/017970, or WO 03/017979 for example. The disclosure of WO 02/30390, WO 03/017970, and WO 03/017979 is hereby incorporated by reference into the instant patent application in its entirety.

As an example, the pharmaceutical compositions according to the invention may be obtained by the method described below.

First, the excipient and the active substance are placed in a suitable mixing container. The active substance used has an average particle size of 0.5 to 10 μm, preferably 1 to 6 μm, most preferably 2 to 5 μm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

If after being chemically prepared the active substance used in the process described above is not already obtainable in a crystalline form with the particle sizes mentioned earlier, it can be ground up into the particle sizes which conform to the above-mentioned parameters (so-called micronizing).

Many modifications and variations of the invention falling within the terms of the following claims will be apparent to those skilled in the art and the foregoing description should be regarded as a description of the preferred embodiments of the invention only.

The invention claimed is:

1. An inhaler comprising a housing containing a strip of blisters each blister being defined by a blister cavity containing a dose of medicament and a puncturable lid, the inhaler including means to sequentially move each blister into alignment with means for puncturing said puncturable lid of a blister to enable a user to inhale said dose through said puncturable lid and, a spiral wound element in the said housing, the blister cavities, together with their punctured lids, being received in said spiral wound element to coil the strip, wherein the housing includes a common chamber to receive an unused blister strip and a used portion of that strip, wherein a flexible dividing wall separates the chamber into a used and unused blister compartment, the flexible dividing wall comprising a foam strip.

2. An inhaler according to claim 1, wherein the flexible dividing wall is fixed to the housing at both ends.

3. An inhaler according to claim 1, wherein the dividing wall is flexible and configured so that it extends across said common chamber between sidewalls of the inhaler to prevent passage of powdered dose between the unused and used blister compartments.

4. An inhaler according to claim 3, wherein the width of the flexible dividing wall is greater than the distance between the sidewalls so that the flexible dividing wall is held in compression between the sidewalls.

5. An inhaler according to claim 1, wherein the foam strip includes a stiffening element.

6. An inhaler according to claim 1, comprising a second spiral wound element to receive an unused blister strip for insertion into the housing during assembly, the arrangement being such that the second spiral wound element retracts as the first spiral wound element expands as the size of the coil formed from a used portion of the strip increases and the size of the coil formed from an unused portion of the strip decreases.

7. An inhaler comprising a housing to receive a strip of blisters, and an actuator to sequentially move each blister into alignment with means for opening a blister to enable a user to inhale a dose, the housing including a chamber to receive used blisters and, the inhaler further comprising an indexing wheel around which emptied blisters are fed and which rotates in response to movement of said actuator to draw the blister strip through the housing and sequentially align each blister with said means for opening a blister, the indexing wheel being configured such that blister cavities are partially squashed between the indexing wheel and a wall of the housing to compress said blister cavities as they pass around the indexing wheel.

8. An inhaler according to claim 7, wherein the indexing wheel comprises a plurality of spokes extending from a hub and the blister strip comprises a plurality of blister cavities each containing a dose of medicament and a lid sealing the dose within said cavities prior to inhalation, the blister cavities being entrained, together with their lids, between the spokes of the indexing wheel such that the blister cavities are sequentially moved into alignment with means for opening a blister in response to rotation of the indexing wheel, the indexing wheel being configured such that a distance between a surface of the hub and a wall of the housing is less than a height of a blister cavity so that the blister cavities and lids are partially squashed between the hub and said wall of the housing as they pass around the indexing wheel.

9. An inhaler according to claim 8, wherein the lid is puncturable and the means for opening the lid of a blister comprises means for puncturing said lid to enable a user to inhale said dose through said punctured lid.

10. An inhaler comprising a housing containing a strip of blisters each having a blister cavity containing a dose of medicament with a puncturable lid extending over and sealing said dose within the blister cavity, and an actuator to sequentially move each blister into alignment with means for puncturing the lid of an aligned blister to enable a user to inhale said dose, the housing including a first compartment to contain unused blisters cavities with their lids intact and a second compartment, separated from the first compartment by a movable dividing wall, to receive used blister cavities together with their punctured lids, the inhaler further comprising an indexing wheel around which the used blister cavities and their punctured lids are fed and which rotates in response to movement of said actuator to draw the blister strip through the housing and sequentially align each unused blister cavity with said means for puncturing a blister, the indexing wheel being configured such that used blister cavities, together with their punctured lids, are partially squashed between the indexing wheel and a wall of the housing to compress said blister cavities and punctured lids as the strip passes around the indexing wheel.

11. An inhaler comprising a housing containing a strip of blisters each having a blister cavity containing a dose of medicament with a puncturable lid extending over and sealing said dose within the blister cavity, and an actuator to sequentially move each blister into alignment with means for puncturing the lid of an aligned blister to enable a user to inhale said dose, the inhaler further comprising an indexing wheel around which the used blister cavities and their punctured lids are fed and which rotates in response to movement of said actuator to draw the blister strip through the housing and sequentially align each unused blister cavity with said means for puncturing a blister, the indexing wheel being configured such that used blister cavities, together with their punctured lids, are partially squashed between the indexing wheel and a wall of the housing to compress said blister cavities and punctured lids as the strip passes around the indexing wheel, a spiral wound element being mounted in the housing such that the compressed blister cavities, together with their punctured lids, are received in the spiral wound element to coil the strip.

12. An inhaler comprising a device having a housing containing a strip of blisters each having a blister cavity containing a dose of medicament with a puncturable lid extending over and sealing said dose within the blister cavity, and an actuator to sequentially move each blister into alignment with means for puncturing the lid of an aligned blister to enable a user to inhale said dose, the housing including a first compartment to contain unused blisters cavities with their lids intact and a second compartment, separated from the first compartment by a movable dividing wall, to receive used blister cavities together with their punctured lids, the inhaler further comprising an indexing wheel around which the used blister cavities and their punctured lids are fed and which rotates in response to movement of said actuator to draw the blister strip through the housing and sequentially align each unused blister cavity with said means for puncturing a blister, the indexing wheel being configured such that used blister cavities, together with their punctured lids, are partially squashed between the indexing wheel and a wall of the housing to compress said blister cavities and punctured lids as the strip passes around the indexing wheel, a spiral wound element being mounted in the second compartment such that the compressed blister cavities, together with their punctured lids, are received in the spiral wound element to coil the strip.

* * * * *